US006855872B2

(12) United States Patent
Harris et al.

(10) Patent No.: US 6,855,872 B2
(45) Date of Patent: Feb. 15, 2005

(54) TOLERANCE OF TRICHOTHECENE MYCOTOXINS IN PLANTS THROUGH THE MODIFICATION OF THE RIBOSOMAL PROTEIN L3 GENE

(75) Inventors: Linda J. Harris, Greely (CA); Stephen C. Gleddie, Ottawa (CA); John A. Simmonds, Ottawa (CA)

(73) Assignee: Her Majesty the Queen in right of Canada, as represented by the Minister of Agriculture and Agri-food, Ottawa (CA)

( * ) Notice: Subject to any disclaimer, the term of this patent is extended or adjusted under 35 U.S.C. 154(b) by 0 days.

(21) Appl. No.: 09/725,957

(22) Filed: Nov. 30, 2000

(65) Prior Publication Data

US 2002/0088022 A1 Jul. 4, 2002

Related U.S. Application Data

(63) Continuation-in-part of application No. 09/567,326, filed on May 9, 2000, now abandoned, which is a continuation of application No. 08/909,828, filed on Aug. 12, 1997, now Pat. No. 6,060,646.

(51) Int. Cl.[7] .............................. A01H 5/00; A01H 5/10; C12N 15/29; C12N 15/82

(52) U.S. Cl. ................... 800/301; 435/320.1; 536/23.6; 800/279; 800/298

(58) Field of Search ............................. 536/23.1, 23.6; 435/320.1, 419; 800/279, 298, 301, 320.2

(56) References Cited

U.S. PATENT DOCUMENTS

| 4,816,406 A | 3/1989 | Desjardins | 514/256 |
|---|---|---|---|
| 5,498,431 A | 3/1996 | Lindner | 415/216.1 |
| 6,060,646 A * | 5/2000 | Harris et al. | 800/301 |

FOREIGN PATENT DOCUMENTS

| WO | WO 94/13790 | 6/1994 |
|---|---|---|
| WO | WO 95/07989 A2 | 3/1995 |
| WO | WO 96/06175 A2 | 2/1996 |
| WO | WO 96/20595 A1 | 7/1996 |
| WO | 96/32007 * | 10/1996 |
| WO | WO96/32007 A1 * | 10/1996 |
| WO | WO 01/05976 A1 | 1/2001 |

OTHER PUBLICATIONS

Kim, Yongcheol 1991, Ribosomal protein gene expression and trichothecene resistance in *Arabidopsis thaliana*. Dissertation Abstracts International 52(28):657.*
Schultz et al 1983, Nucleotide sequence of the tcm1 gene (ribosomal protein L3) of *Saccharomyces cerevisiae*. Journal of Bacteriology 155(1):8–14.*
Bohn et al, Genbank Accession No. Z74971, submitted Jul. 4, 1996.*
Kim et al 1990, Two evolutionary divergent genes encode a cytoplasmic ribosomal protein of *Arabidopisis thaliana*. Gene 93:177–182.*
Bosch et al 1994, A trout growth hormone is expressed, correctly folded and partially glycosylated in the leaves but not the seed of transgenic plants. Transgenic Research 3:304–310.*
Kim et al., Two evolutionarily divergent gene encode a cytoplasmic ribosomal protein of *Arsbidopsis thaliana*, 1990, Gene, vol. 93, pp. 177–182.*
Schultz et al., Nucleotide Sequence of the tcml Gene (Ribosomal Protein L3) of *Saccharomyces cerevisiae*, Jul. 1983, Journal of Bacteriology, vol. 155, No. 1, pp. 8–14.*
Bosch et al., A trout growth hormone is expressed, correctly folded and partially . . . 1994, Transgeneic Research, vol. 3, pp. 304–310.*
Youngchedl et al., XP–002083007.*
Nishi, R. et al., " The Primary Structure of Two Proteins From The Large Ribosomal Subunit of Rice", Biochimica et Biophysica Acta, 1993, 1216: 110–112.
Shultz, L.D. and Friesen, J.D. "Nucleotide Sequence of the tcm1 Gene (Ribosomal Protein L3) of *Saccharomyces cerevisiae*", Journal of Bacteriology, Jul. 1983, 155:8–14.
Fried, H. M. and Warner, J.R. " Cloning of Yeast Gene For Trichodermin Resistance and Ribosomal protein L3", Proc. Natl. Acad. Sci. USA, Jan. 1981, 78,No. 1, 238–242.
Grant, P.G. et al. "Mapping of Trichodermin Resistance In *Saccharomyces cerevisiae*: A Genetic Locus for A Component of the 60S Ribsomal Subunit", Genetics, Aug. 1976, 83:667–673.
Picard–Bennoun, M. and Le Coze D., "Search for Ribosomal Mutants In Podospora–Anserina Genetic Analysis of Cold Sensitive Mutants", Biological Abstracts, 1980, vol. 72, No. 2691.
Kim, Y. et al., "Two Evolutionarily Divergent Genes Encode a Cytoplasmic Ribosomal Protein of *Arabidopsis thaliana*", 1990, Gene, 93:177–182.

(List continued on next page.)

Primary Examiner—David H Kruse
(74) Attorney, Agent, or Firm—Rothwell Figg Ernst & Manbeck

(57) ABSTRACT

*Fusarium graminearum* is a plant pathogen, attacking a wide range of plant species including corn (ear and stalk rot), barley, and wheat (head blight). *Fusarium* epidemics result in millions of dollars of losses in crop revenues. *Fusarium graminearum* infection in the cereals reduces both grain yield and quality. Mycotoxins are produced by many fungal *Fusarium* species and thus the grain becomes contaminated with these mycotoxins, such as the trichothecenes. The major trichothecene produced by *F. graminearum* is deoxynivalenol (abbreviated as DON, also known as vomitoxin). Trichothecenes are potent protein synthesis inhibitors and are quite toxic to humans and livestock. A yeast gene has been identified which confers upon yeast tolerant of the trichothecene, trichodermin. A corresponding plant gene has been prepared, which has been used to transform plants. These transformed plants have an increased resistance to *Fusarium* infestation.

13 Claims, 18 Drawing Sheets

OTHER PUBLICATIONS

Schindler, D. et al., "Trichodermin Resistance–mutation Affecting Eukaryotic Ribosomes", 1974, Nature 248:535–536.

de la Fuente–Martinez, J.M. et al. "Expression of a Bacterial Phaseolotoxin–Resistant Ornithyl Transcarbamylase in Transgenic Tobacco Confers Resistance to *Pseudomonas syringae* pv. Phaseolicola", Aug. 1992, Biotechnology, 10:905–909.

Kim. Y. and Scholl R.L..., "Ribosomal Protein Gene Expression and Trichothecene Resistance in *Arabidopsis thaliana*", 1991, Dissertation Abstracts International, 91:4157, Dissertation, Ohio State University.

Zeisler, J., "Analysis of Gene Clones Thought to Code for *Saccharomyces cerevisiae* Ribosomal Proteins and Construction of a Plasmid Vector Suitable for Gene Cloning in Yeast", 1981, Masters Abstracts International, 96:8168, York University.

Trapp, S.C. and Jarvis, B, Isolation and Characterization of *Macrocyclic Trichothecene* Biosynthetic Pathway Genes from *Myrothecium Roridum*: A Case Study for Horizontal Gene Transfer (Fungi, *Baccharis Megapotamica, Baccharis Coridifolia, Fusarium Sporotrichioides*), 1997, Dissertation Abstracts International 97:71410.

Posselt, U.K. and Altpeter F., "Improvement of Snow Mould Resistance by Conventional and In Vitro Techniques", 1994, Euphytica, 77:251–255.

Miedaner, T., "Breeding Wheat and Rye for Resistance to Fusarium Diseases", 1997, Plant Breeding 116:201–220.

Lemmens, M., et al. "Breeding for Head Blight (Fusarium SPP.) Resistance in Wheat: Development of A Mycotoxin-Based Selection Method of Seedlings", 1994, Acta Horticulturae, Plant Breeding for Mankind, 355:223–232.

Bruins, M.B.M. et al. "Phytotoxicity of Deoxynivalenol to Wheat Tissue With Regard To In Vitro Selection Fusarium Head Blight Resistance", 1993, Plant Science 94:195–206.

Snijders, C.H. A. and Krechting, C.F. "Inhibition of Deoxynivalenol Translocation and Fungal Colonization in Fusarium Head Blight Resistant Wheat", Jan. 1992, 70:1570–1576.

Miller J.D. and Ewen, M.A. "Toxic Effect of Deoxynivalenol on Ribosomes and Tissues of the Spring Wheat Cutitvars Frontana and Casavant", 1997, Nat. Toxins, (Abstract) 5:234–237 PMID:9615311.

* cited by examiner

FIGURE 1

SCRPL13PWT - MSHRKYEAPRHGHLGFLPRKRAASIRARVKAFPKDDRSKPVALTSFLGYK
SCRP13PRO  - MSHRKYEAPRHGHLGFLPRKRAASIRARVKAFPKDDRSKPVALTSFLGYK

SCRPL13PWT - AGHTTIVRDLDRPGSKFHKREVVEAVTVVDTPPVVVGVVGYVETPRGLR
SCRP13PRO  - AGHTTIVRDLDRPGSKFHKREVVEAVTVVDTPPVVVGVVGYVETPRGLR

SCRPL13PWT - SLTTVWAEHLSDEVKRRFYKNWYKSKKKAFTKYSAKYAQDGAGIERELAR
SCRP13PRO  - SLTTVWAEHLSDEVKRRFYKNWYKSKKKAFTKYSAKYAQDGAGIERELAR

SCRPL13PWT - IKKYASVVRVLVHTQIRKTPLAQKKAHLAEIQLNGGSISEKVDWAREHFE
SCRP13PRO  - IKKYASVVRVLVHTQIRKTPLAQKKAHLAEIQLNGGSISEKVDWAREHFE

SCRPL13PWT - KTVAVDSVFEQNEHIDAIAVTKGHGFEGVTHRWGTKKLPRKTHRGLRKVA
SCRP13PRO  - KTVAVDSVFEQNEHIDAIAVTKGHGFEGVTHRNGTKKLPRKTHRGLRKVA

SCRPL13PWT - CIGAWHPAHVMWSVARAGQRGYHSRTSINHKIYRVGKGDDEANGATSFDR
SCRP13PRO  - CIGA[C]HPAHVMWSVARAGQRGYHSRTSINHKIYRVGKGDDEANGATSFDR

SCRPL13PWT - TKKTITPMGGFVHYGEIKNDFIMVKGCIPGNRKRIVTLRKSLYTNTSRKA
SCRP13PRO  - TKKTITPMGGFVHYGEIKNDFIMVKGCIPGNRKRIVTLRKSLYTNTSRKA

Broad host range plasmid Bin 19, complete sequence.
11777 bp

FIGURE 7B

```
                         190       200       210       220       230       240       250       260       270
                GAGAAGCCTGGTTCCAAGCTCCACAGAAGAAGAAACTTGTGAGGCTGTGTACCATCATTGAGACCCCTCCTCTGTCATTGTTGGACTTGTG
maize1.SEQ      GAGAAGCCAGGATCCAAACTCCATAAGAAGAAACTTGTGAGGCTGTGTACCATCATTGAAACCCCTCCTCTTGTCATTGTTGGGCTCGTG  270
maize2.SEQ      GAGAAGCCAGGATCCAAACTCCATAAGAAGAAACTTGTGAGGCTGTGTACCATCATTGAAACCCCTCCTCTTGTCATTGTTGGGCTCGTG  270
sorghum1.seq    GAGAAGCCTGGATCCAAACTACACAGAAGAAGAAACGTGTGAGGCTGTGTACCATCATTGAAACCCCTCCTCTCGGTCATTGTTGGCTTGTG  270
sorghum2.seq    GAGAAGCCTGGCTCCAAGCTCCACAGAAGAAGAAACTTGTGAGGCTGTGTGACTATCATTGAGACCCCTTGTCATTGTCGGACTTGTG  270
wheat.seq       GAGAAGCCTGGTTCCAAGCTACACAGAAGAAGAAGAAGACATGTGAGGCTGTGCACCATTGTTGAGACACCCCGATTGTATTGTTGGACTTGTT  270
barley.seq      GAGAAGCCTGGTTCCAAGCTGCACAAGAAGAAGAAGAAGACATGTGAGGCTGTGCACCATTGTTGAGACACCCCTATTGTTATTGTTGGACTTGTT  270
oat.seq         -----GCCTGGTTCAAAGCTACACAGAAGAAGAAGAAACGAGAGGCTGAGCCGTGACCTGTTACCACAATTGTTATTGTTGTTGGACTTGTT  93
rice.SEQ        GAGAAGCCTGGCTCCAAGCTCGCCAGTGCGGAGGCTGTTACCATCATCGAGACCCCTCCGCTTGTCATTGTTGTTGGACTCGTG  270

280       290       300       310       320       330       340       350       360
                GCCTATGTGAAGACTCCTCGTGGCCTTCGCACTCTCAACTCTGTCTCGGCCCAGCATCTTAGCGAGAAGTGAGGAGAAGTTCTACAAG
maize1.SEQ      GCATATGTGAAGACTCCTCGTGGCCTCGGCACACCCAACTCTGTTTGGGCCCAACATCTTAGCGAAGAAGTGAGGAGAAGTTCTACAAG  360
maize2.SEQ      GCATATGTGAAGACTCCTCGGCCTGGCCTCCGCACACTCAACTCTGTTTGGGCCCAACATCTTAGCGAAGAAGTGAGGAGAAGTTCTACAAG  360
sorghum1.seq    GCATATGTGAAGACTSCTCGCGGGCCTCCGCACACTCAACACTGTTTGGGCTCAGCATCTTAGCGAAGAAGTTAGGAGAAGTTCTACAAG  360
sorghum2.seq    GCATATGTGAAGACTCCTCGGGCCTGGCCTCGCACACCCTCAACTCTGTCTCGGCCCAGCACCTTAGTGAAGAAGTGAGGAGAAGTTTTACAAG  360
wheat.seq       GCCTATGTGAAGACTCCTCGTGGCCTTCGTACTCTCAACTCTGTCTCGGCACACAGACATCTCAGCGAAAATGTSAGGAGAAGTTCTACAAG  360
barley.seq      GCCTATGTGAAGACTCCTCGTGGCCTTCGTACTCTCAACTCTGTCTCGGGCACACAGACATCTCAGCGAAGATGTGAGGAGAAGTTCTACAAG  360
oat.seq         GCCTACGTGAAGACTCCTCGTGGCCTTCGCACTCTTAACACTGTCTCAGCATCGTGGGCTCAGAGACGTTAGGAGACGTTAGAGGAGTTCTACAAG  183
rice.SEQ        GCCTATGTCAAGACACCTCGTGGACTTCGCTCTCTCAACTCGTCTCTGGGCCCAGCACCTTAGCGAGGAGGTGCGGAGAAGTTCTACAAG  360
```

FIGURE 7C

```
             370        380        390        400        410        420        430        440        450
              |          |          |          |          |          |          |          |          |
maize1.SEQ   AACTGGTGCAAGAGCAAGAAGAAGGCTTTCACCAAGTACTCTCAAGTATGCTCTCAAGTATGACAGTGATGCTGGCAAGAAGGAAATTCAGCTGCAGCTT  450
maize2.SEQ   AACTGGTGCAAGAGCAAGAAGAAGGCTTTCACCAAGTACTCTCAAGTATGCTCTCAAGTATGACAGTGATGCTGGCAAGAAGGAAATTCAGCTGCAGCTT  450
sorghum1.seq AACTGGTGCAAGAGCAAGAAGAAGGCTTTCTCCAAGTACTCTCAAGTATGCTCTCAAGTATGACAATGATGCTGGCAAGAAGGAAATTCAGCTGCAGCTT  450
sorghum2.seq AACTGGTGCAAGAGCAAGAAGAAGGCCCTTCACCAAGTACGCCCTTCAAGTATGCTGACGCCAGGCAGGCAAGAAGAAATCAGTTGCAGCTT          450
wheat.seq    AACTGGTGCAAGAGCAAGAAGAAGGCCCTTCACCAAGTACTCTGAAGTATGCTCTGAAGTATGACAGTGATGCTGGCAAGAAGAAATCAGATGCAGCTT  450
barley.seq   AACTGGTGCAAGAGCAAGAAGAAGGCCTTCACCAAGTATGCGCTGAAGTATGCTCTCAAGTATGACAGTGATGCAGGCAAGAAGAAATCAGATGCAGCTT 450
oat.seq      AACTGGTGCAAGAGCAAGAAGAAGGCTTTCACCAAGTCTCTCAAGTATGCCCTTAAGTATGACAGTGATGCTGCAGGCAAGAAGGAAATTCAGCTGCAGCTT 273
rice.SEQ     AACTGGTGCAAAAGCAAGAAGAAGGCTTTCACTAAGTACTCTTAAGTATGCCCTTAAGTATGATGATGCTGATGCTGGCAAGAAGAAGAAATCCAGATGCAACTT 450

460        470        480        490        500        510        520        530        540
               |          |          |          |          |          |          |          |          |
maize1.SEQ   GAGAAGATGAAGAAGTATGCTTCTTCTGTTGTCCGTGTTATTGCCCATACCCAGATTAGGAAGATGAAGGCTTTGAAGCAGAAGAAGGCTCAC         540
maize2.SEQ   GAGAAGATGAAGAAGAAATATGCTTCTTCTGTTGTCCGTGTTATTGCCCATACCCAGATTAGGAAGATGAAGGGTTTGAAGCAGAAGAAGGCTCAC      540
sorghum1.seq GAGAAGATGAAGAAGAAATATGCTTCTTCGTGTTCGTGTCCGTGTCATTGCCCATACCCAGATTAGGAAGATGAAGGGTTTGAAGCAGAAGAAGGCTCAC 540
sorghum2.seq GAGAAGATGAAGAAGTATGCTTCAGTTGATCCGTGTTATCCGCACACTCAGATTAGCCCATACCCAGATTAAGAAGATGAAGGGTTTGAAGCAGAAGGCTCAT 540
wheat.seq    GAGAAGATGAAGAAGTATGCTTCTGTTGTCCGAGTTATCGCCCATACCCAGATCCAGATTAAAAAGATGAAAGGTTGAAGCAGAAGAAGGCTCAC       540
barley.seq   GAGAAGATGAAGAAGTATGCTACTGTTGTCCGAGTTATCGCCCATACCCAGATCAGGAAGATGAAGGGTTGAAGCAGAAGAAGGCTCAC             540
oat.seq      GAGAAGATGAAGAAGTATGCACTGTATCGGTAATCGCCCATTATCGCCCATACCCAGATAAGGAAGATGAAGGGGCTGAAGCAGAAGAAGGCTCAC     303
rice.SEQ     GAGAAGATGAAGAAGTACGCCATCTATTGTTCGTGTTATTGCCCACACTCAGATCCAGATCAGAAGATCAGAAGATGAAGCAGAAGAAGGCTCAC      540
```

FIGURE 7D

```
              CTCATGGAGATCAGGTCAATGTGCCACCATTGCTGACAAGGTGACTATGGCTACAAATTCTTGAGAAGGAAGTCCCTGTTGATGCT
                        560         570         580         590         600         610         620       630 maize1.SEQ   CTGATGGAGATTCAGGTCAATGTGTGCCACCATTGCTGACAAGGTGACTATGGCTACAAATTTTTGAGAAAGACCTCCCTGTTGATGCT   630
maize2.SEQ   CTGATGGAGATTCAGGTCAATGTGTGCCACCATTGCTGACAAGGTGACTATGGCTACAAATTCTTTGAGAAAGAGGTCCCTGTTGATGCT  630
sorghum1.se  CTCATGGAGATTCAGGTCAATGTGGTACCATTGCTGACAAGGTGGA                                             587
sorghum2.seq CTTATGGAGATCAGGTCAATGTGGCACTATAGCGACAAGCAGACAAGGTGACTATGGTTACAAATTCTTGAGAACGAAGTTCCTGTTGATGCT 630
wheat.seq    CTCATGGAGATCAGGTCAATGTGGCACCATCGCTGACAAGGTGACTATGGTTACAACTTCTTTGAGAAGGAAGTCCCCATTGATGCT   630
barley.seq   CTCATGGAGATCAGGTCAATGTGGCACCATTGCCGATAAGGTGGACTATGGTTACAAGTTCTTTGAGAAGGAAGTCCCCATTGATGCG   630
oat.seq      CTGATCGAGATCAGGTCAATGTGGCACCATCGCAGACAAGGTGACTATGGCTACAAATTTCTTGAGAAGGAAGTCCCCATTGATGCT   453
rice.SEQ     CTCATGGAGATCAGGTCAATCAACGTGGCACTATCGCCGACAAGGTGACTATGGCTACAAGTTCTTTGAGAAGGAAATCCCTGTTGATGCA   630
```

```
              GTCTTCCAGAAGGATGAGATGATTGACATCATTGGTGTGACCAAGGTAAGGGTAAGGGTAAAAGGTTATGAGGGTGTGGTCACTCGTCACCCGC
                        640         650         660         670         680         690         700         710      720 maize1.SEQ   GTCTTCCAGAAGGATGAGATGATTGACATCATTGGTGTGACCAAGGTAAAAAGGTTATGAGGGTGTGGTCACTCGTGGGGTGTCACCCGG   720
maize2.SEQ   GTCTTCCAGAAGGATGAGATGATTGACATCATTGGTGTGACCAAGGGAAAAGGTTATGACGGGTGTGGTCACTCGTCGTGGGGTGTCACCCGG   720
sorghum1.seq                                                                                              587
sorghum2.seq GTGTTCCAGAAGGATGAGATGATTGACATCATTGGAGTCACCAAGGGTAAGGGGTATGAAGGTGTCACTCGTTGGGGTGTACCCGG   720
wheat.seq    GTATTCCAAAAAGATGAGATGATTGACATCATTGGAGTTACCAAGGGTAAGGGTTATGAAGGTGTTGTGACACGTTGAAGGTGTCACCCGT   720
barley.seq   GTTTTCCAAAARGATGAGATGATTGATATCATTGGTGTAACCAAGGGTAAGGGTTATGAAGGTGTGTGACACGTTGACACGTTGGGGTGTCACCCGC   720
oat.seq      GTCTTCCAGAGGATGATGATTGACATTGGTGTCACTAAGGGTAAGGGTTATGAAGGTGTGACACGTTGGGGTGTCACCCGC   543
rice.SEQ     GTCTTCCAGAAGGACGAGATGATTGACATCATTGGTGTCACTAAGGGTAAGGGTTATGAAGGTGTCGTCACTCGTGAAGGTGTCGTCACCCGC   720
```

FIGURE 7E

```
              CTTCCCCGCAAGACCCACAGGGGTCTCCGCAAGGTTGCCTGTATTGGTCCTGGCATCCGCTAGGGTCTCCTATACGGTTGCCCGTGCT
              730         740         750         760         770         780         790         800         810
```

| | |
|---|---|
| maize1.SEQ | CTTCCCCGCAAAACCCACAGGGGTCTCCGCAAGTTGCTTGTATGGTCATGGCATCCGGCTAGGTCTCCTATACGGTTGCCCGTGCT 810 |
| maize2.SEQ | CTTCCCCGCAAGACCCACAGAGGGTCTCCGCAAGTTGCTTGTATGGTCATGGCATCCGGCATGGTCTCCTATACGGTTGCTGTGCT 810 |
| sorghum1.seq | 587 |
| sorghum2.seq | CTTCCCCGCAAGACCCACAGGGGTCTCCGCAAGGTTGCCTGTATTGCGCCTGGCATCCAGCTAGGGTGTCGTACACAGTTGCCCGCGCT 810 |
| wheat.seq | CTTCCCCGCAAGACCCACAGAGGTCTTCGCAAGGTTGCCTGTATTGGTGCCTGGCATCCTGCTAGGGTGTCCTACACTGTTGCTCTGCT 810 |
| barley.seq | CTTCCCCGCAAGACCCACAGAGGTCTCCGCAAGGTTGCCTGTATTGTGCCTGGCATCCTGCTAGGGTGTCCTACACTGTTGCTCTGCT 810 |
| oat.seq | CTTCCCCGCAAGACCCACAGAGGTCTCCGCAAGGTTGCCTGTATTGGTGCCTGGCATCCTGCTAGGGTGTCCTACACTGTTGCCGGCT 633 |
| rice.SEQ | CTTCCTCGCAAGACCCACAGGGGTCTCCGCAAGGTTGCTTGTATTGGTGCCTGGCATCCAGCCAGGGTGTCCTACACTGTTGCCCTGCT 810 |

```
              GGTCAGAATGGATACCACCACCGCCACTGAGATGAACAAGAAGTTTACAAGATCGGGACAAGGAGACCCATGATGCCTCCACT
              820         830         840         850         860         870         880         890         900
```

| | |
|---|---|
| maize1.SEQ | GGTCAGAATGGGTACCACCACCGCCACTGAGATGAACAAGAAGTCTACAAGATCGGGACAAGGACCCACGATGCCTCCACA 900 |
| maize2.SEQ | GGTCAGAATGGGTACCACCACCGCCACTGAGATGAACAAGAAGTTTACAAGATCGGACAAGGCTGACAAGAGACCCACGATGCCTCCACA 900 |
| sorghum1.seq | 587 |
| sorghum2.seq | GGTCAGAATGGATACCATCACCGTACTGAGATGAACAAGAAGTTTACAAGATGAACAAGGCTGGAAGGCTGGACAGGAGAGCCATGATGCCTCAACT 900 |
| wheat.seq | GGTCAGAATGGATACCACCACCGCCACTGAGATGAACAAGAAGTCTACAAGATTGGCAAGGTTGACAGGAGAAACTCATGATGCCTCTACT 900 |
| barley.seq | GGTCAGAATGGATACCACCACCGCCACTGAGATGAACAAGAAGTGTACAAGATTGGCAAGGTTGMCAGGAGACCCATGATGCCTCCACA 900 |
| oat.seq | GGTCAGAATGGATACCACCACCGACACTGAACTGAACAAGAAGATTACAAGATCGGCAAGGTTGGACAGGAGAACTCATGATGCCTCTACT 723 |
| rice.SEQ | GGTCAGAACGGATACCACCACCGCCACTGAATGAACAAGAAGTTTACAAGATTGGCAAGTCTGGTCAGGAGTCTCATGCGGGCCTGCACC 900 |

FIGURE 7F

```
                    910       920       930       940       950       960       970       980
             GAGTTCGACAGGACTGAGAAGGACATCACTCCCACTATGGGTGGCTTCCCCACTATGGTGTGGTGAAGGGTGACTACCTGATGATCAAGGGA
maize1.SEQ   GAGTTTGACAGGACTGAGAAGGACATCACTCCCATGGGTGGCTTCCCCACTATGGTGTGAAGGGTGACTACCTGATGATCAAGGGC     990
maize2.SEQ   GAGTTTGACAGGACTGAGAAGGACATCACTCCCATGGGTGGCTTCCCCATTATGGTGTGAAGGGTGACTACCTGATGATCAAGGGC     990
sorghum1.seq                                                                                     587
sorghum2.seq GAGTTTGACAGGACTGAGAAGGACATCACTCCCATGGGTGGCTTCCCCACTATGGTGTTGTCAAAGGTGACTACCTGATGATCAAGGT    990
wheat.seq    GAGTTCGACAGGACCGAGAAGGACATCACTCCGATGGGTYGGCTTCCCCACTATGGTGTGGTGAAGGCTGACTACCTGATGATCAAGGA    990
barley.seq   GAGTTCGACAGGACCGAGAAGGACATCACTCCCATGGGTGGCTTCCCCACTATGGTGTGGTGAAGGCCGACTACCTGATGATCAAGGA    990
oat.seq      GAGTTCGACAGGACTGAGAAGGACATCACCCCCATGGGTGGCTGGCTTCCCCACTACGGTGTGAAGGGTGACTACCTCATGATCAAGGA    813
rice.SEQ     GAGTTCGACAGGACTGAGAAGGACATCACCCCCGATGGGCGGCTTCCCCACTACGGTGTGGTGAAGGGCGACTACCTCATGATCAAGGT    990

1000      1010      1020      1030      1040      1050      1060      1070      1080
             TGCTGTGTCGGTCGGTCAAAGAAGAGGGTGGTGCAGTCCTCCCCAGTCCCTCCTGAAGCAGACCTCCGCTGGCCCTGAAGATCAAGCTC
maize1.SEQ   TGCTGTGTGGGTCCAAA-AAGAGGGTGGTGACGTTCCCGCAGTCCCTCCTGAAGCAGACTTCCGCTGGCCTGGCGCTGGAGGAGATCAAGCTC   1079
maize2.SEQ   TGCTGTGTGGGTCCAAAGAAGAGGGTGGTGACGTTCCCGCAGTCCCTCCTGAAGCAGACTTCCGCTGGCCTGGCGCTGGAGGAGATCAAGCTC   1080
sorghum1.seq                                                                                              587
sorghum2.seq TGCTGCGTTGGCCCAAGAAGAGGGTGGTGACTCTCCGCGTGACTCTCTGAAGCAGACCTCTCGCTGGCCTGGCTCTGGAGGAGATCAAGCTC    1080
wheat.seq    TGCTGTGTCGCCCCCAAGAAGCGGGTGGTGTGTGACTCTCCGCCCTCCTGAAGCAGAACCCTTCGCTGTCTTCGGCCCGTCTCTGGAGGAGATCAAGCTC 1080
barley.seq   TGCTGTGTCGGGCCAAAGAAGAGGCGTGTGACGTCTCCGCCCTCCTGAAGCAGACAGACCTGTCGCTCTCCACTGAGGGCCTGAGGAGATCAAGCTC    1080
oat.seq      TGCTGCGTTGGCCGTCCGAAGAAGAGAGTGTGGTGTCACCCCGACCCTCCGCCCTCCTGAAGCAGACAGACCCGTCGCCGTCTGGCCCTGGAGGAGAAATCAAGCTC    903
rice.SEQ     TGCTGCGTCGGTCCGAAGAAGAGAGTGTGGTGTCACCCCGACCCTCCGCCCTCCTGAAGCAGACAGACCTCGCCGGCTCGCCGGGCCCTGAGGAGGATCAAGCTC    1080
```

FIGURE 7H

```
                 1270      1280      1290      1300      1310      1320      1330      1340      1350
             TTTGTA--T-CTGATGTTTTG-TAGTCTG-GCCGTTTATGAAT-GGATGTTCATGTGCTG-G----TATGG-TTGCAAATTXXAXXXXX
maize1.SEQ   --TGTA--C-CAAGT--TTTG-TAGCC---------------------GGATGGTTCG-------G-G-----CACGG-TCGC---TT      1281
maize2.SEQ   --TGTA--C-CAAGT--TTTG-TAGCC---------------------GGATGGTTCG-------G-G-----CACGG-TCGC---TT      1282
sorghum1.seq                                                                                         587
sorghum2.seq AACATG--T-TTGAT--TTTC-TAGTCTGAGCTACTTCCATTGCGGATGATTGA--TATTG-A----TATTA-TTGCAAATC--          1329
wheat.seq    TTTGTACTAGKTGATGTTTTCAGAATCTGGCTCATCTATGAATTCTTCGTGTCATGTGCTAYTGTTATTGTGATTTAGCTGTTGAAACCT    1338
barley.seq   TTG------AGCTGGGGTGDCAMGAATC--ATCTTMTATGAAA-----GGGGCATGGGCYRTGDGTTTGGAATWAAAATDDGGAAAA--    1314
oat.seq      TTTGTA---GCTGACTTTTTAAGAATCTG-TCCGTCTATGAATTCTT--GTCATGTGCTA------------AAAAAAAAAA---        1139
rice.SEQ     TACCCAGTT-TAAATGCTTTGCTACTCTGAGCTGCTGGTGCTGCGGATGATCAAACTGTTG-AGATTTATGAATTTGAACTCGATAGTT    1340
```

```
             XXXXXXX
maize1.SEQ                  1281
maize2.SEQ                  1282
sorghum1.seq                587
sorghum2.seq -TG            1330
wheat.seq    M-GTGCG        1344
barley.seq   A-AAAAA        1315
oat.seq      A-AAAAA        1144
rice.SEQ     ATGTTTT        1347
```

FIGURE 8A

```
              *  *  *            *  *  ** *          * *
maize      MSHRKFEHPRHGSLGFLPRKRSSRHRGKVKSFPRDDPKKPCHLTAFL    47
sorghum    MSHRKFEHPRHGSLSFLPNKRSSRHRGKVKSFPRDDPKKPCHLTAFV
wheat      MSHRKFEHPRHGSLGFLPRKRSSRHRGKVKSFPRDDQSKPCHLTAFL
barley     MSHRKFEHPRHGSLGFLPRKRCSRHRGKVKAFPRDDQSKKCHLTAFL
oat        ................................................
rice       MSHRKFEHPRHGSLGFLPRKRSSRHRGKVKSFPKDDVSKPCHLTSFV

* * *                        *    *
maize      GYKAGMTHIVREVEKPGSKLHKKETCEAVTIIETPPLVIVGLVAYVKT   95
sorghum    GYKAGMTHIVREVEKPGSKLHKKETCEAVTIIETPPLVIVGLVAYVKT
wheat      GYKAGMTHIVREVEKPGSKLHKKETCEAVTIVETPPLVIVGLVAYVKT
barley     GYKAGMTHIVREVEKPGSKLHKKETCEAVTIVETPPIVIVGLVAYVKT
oat        ....................WHEPGSKLHKKETCEAVTIVETPPIVIVGLVAYVKT
rice       GYKAGMTHIVREVEKPGSKLHKKETCEAVTIIETPPLVIVGLVAYVKT

* *         *                                  **
maize      PRGLRTLNSVWAQHLSEEVRRRFYKNWCKSKKKAFTKYALKYENDA   141
sorghum    PRGLRTLNSVWAQHLSEEVRRRFYKNWCKSKKKAFTKYALKYDSDA
wheat      PRGLRTLNSVWAQHLSEDVRRRFYKNWCKSKKKAFTKYALKYDSDA
barley     PRGLRTLNSVWAQHLSEDVRRRFYKNWCKSKKKAFTKYALKYDSDA
oat        PRGLRTLNTVWAQHLSEDVRRRFYKNWCKSKKKAFTKYALKYDSDA
rice       PRGLRSLNSVWAQHLSEEVRRRFYKNWCKSKKKAFTKYALKYDSDA

*         ** * *        *                       *
maize      GKKEIQLQLEKMKKYASV IRVIAHTQIRKMKGLKQKKAHLMEIQVNG 188
sorghum    GKKEIQLQLEKMKKYASV IRVIAHTQIKKMKGLKQKKAHLMEIQVNG
wheat      GKKEIQLQLEKMKKYASVVRVIAHTQIRKMKGLKQKKAHLMEIQVNG
barley     GKKEIQMQLEKMKKYATVVRVIAHTQIRKMKGLKQKKAHLMEIQING
oat        GKKEIQLQLEKMKKYGTV IRVIAHTQIRKMKGLKQKKAHLMEIQVNG
rice       GKKEIQMQLEKMKKYASI VRVIAHTQIRKMKGLKQKKAHLMEIQING

*    *  *[
maize      GTIADKVDYGYKFFEKEVPVDAVFQKDEMIDIIGVTKGKGYEGVVTR 235
sorghum    GTIADKVDYGYKFFEKEVPVDAVFQKDEMIDIIGVTKGKGYEGVVTR
wheat      GTIADKVDYGYNFFEKEVPVDAVFQKDEMIDIIGVTKGKGYEGVVTR
barley     GTIADKVDYGYNFFEKEVP IDAVFQKDEMIDIIGVTKGKGYEGVVTR
oat        GTIADKVDYGYNFFEKEVP IDAVFQKDEMIDIIGVTKGKGYEGVVTR
rice       GTIADKVDYGYKFFEKE IPVDAVFQKDEMIDIIGVTKGKGYEGVVTR
```

FIGURE 8B

```
maize    WGVTRLPRKTHRGLRKVACIGAWHPARVSYTVARAGQNGYHHRTE  280
sorghum  WGVTRLPRKTHRGLRKVACIGAWHPARVSYTVARAGQNGYHHRTE
wheat    WGVTRLPRKTHRGLRKVACIGAWHPARVSYTVARAGQNGYHHRTE
barley   WGVTRLPRKTHRGLRKVACIGAWHPARVSYTVARAGQNGYHHRTE
oat      WGVTRLPRKTHRGLRKVACIGAWHPARVSYTVARAGQNGYHHRTE
rice     WGVTRLPRKTHRGLRKVACIGAWHPARVSYTVARAGQNGYHHRTE

*    *  * *                            *  * maize    MNKKVYKIGKAGQETHDASTEFDRTEKDITPMGGFPHYG IVKGDYL  326
sorghum  MNKKVYKIGKAGQESHDASTEFDRTEKDITPMGGFPHYG IVKGDYL
wheat    MNKKVYKIGKVGQETHDASTEFDRTEKDITPMGGFPHYGVVKGDYL
barley   MNKKVYKIGKVGQETHDASTEFDRTEKDITPMGGFPHYGVVKADYL
oat      MNKK IYKIGKVGQETHDASTEFDRTEKDITPMGGFPHYGVVKGDYL
rice     MNKKVYKIGKSGQESHAACTEFDRTEKDITPMGGFPHYGVVKGDYL

* *   *    * maize    MIKGCCVGPKKRVVTLRQSLLKQTSRLALEEIKLKF IDTSSKFGHGRF  374
sorghum  MIKGCCVGPKKRVVTLRQSLLKQTSRLALEEIKLKF IDTSSKFGHGRF
wheat    MIKGCCVGPKKRVVTLRQSLLKQTSRLALEEIKLKFVDTSSKFGHGRF
barley   MIKGCCVGPKKRVVTLRQSLLKQTSRLALEEIKLKLXDTSFKFGHGPF
oat      MIKGCCVGPKKRVVTLRQSLLKQTSRLALEEIKLKFVDTSSKFGHGRF
rice     MIKGCCVGPKKRVVTLRQSLLKQTSRLALEEIKLKF IDTSSKFGHGRF

*    *  *   *  ***** maize    QTTDEKQRFFGKLKA    389
sorghum  QTTDEKQKFYGKQKA
wheat    QTTDEKQRFFGKLKA
barley   QDTDEKQRFFGKLKAELLGI
oat      QTTDEKQRFYGKLKA
rice     QTTDEKQRFFGKLKA
```

TOLERANCE OF TRICHOTHECENE MYCOTOXINS IN PLANTS THROUGH THE MODIFICATION OF THE RIBOSOMAL PROTEIN L3 GENE

CROSS-REFERENCE TO RELATED APPLICATIONS

The present application is a continuation-in-part application of U.S. patent application Ser. No. 09/567,326 filed on May 9, 2000, now abandoned, which in turn is a continuation application of U.S. patent application Ser. No. 08/909,828, filed on Aug. 12, 1997, now U.S. Pat. No. 6,060,646.

The present invention relates to a modified nucleic acid, wherein a host transformed with said nucleic acid is resistant to trichothecene mycotoxins, wherein the wild type form of said nucleic acid encodes a ribosomal protein L3. The present invention also relates to a method of using said nucleic acid to transform plants to provide increased resistance against trichothecene mycotoxins. The present invention further relates to a method of using the gene as a selectable marker in transformation.

BACKGROUND OF THE INVENTION

Globally, *Fusarium graminearum* is an important plant pathogen, attacking a wide range of plant species including many important crop plants such as corn (ear and stalk rot), barley, rice, oats and wheat (head blight). Favourable environmental conditions (conducive temperatures and high humidity) can result in Fusarium epidemics and millions of dollars lost in crop revenues. *F. graminearum* infection in the cereals reduces both the yield and quality of the grain. The reduction of quality is a result of the mycotoxins produced by this species of fungus; these fungal toxins remain in the contaminated cereal after harvest and pose serious health risks to animals and humans who may consume the grain.

Low levels of contamination in non-epidemic years still account for 5% grain losses to Ontario corn farmers, a figure which translates into approximately $27 Million to the swine industry which uses this corn for feed. In epidemic years, this dollar figure can double or triple. These direct losses to growers include the crop and animal losses associated with reduced feed and poorer quality feed. Overall, the FOA of the United Nations estimates that 25% of the world's food crops are affected by mycotoxins each year (Mannon and Johnson, 1985, Fungi down on the Farm, New Scientist 105: 12–16). *Fusarium* mycotoxins are found in all the major cereal species including corn, wheat, barley, oats, rye and others. The disease is most prevalent in temperate climates.

Mycotoxins, or fungal toxins, are produced by many species of fungi. The species *Fusarium graminearum* as well as *F. sambucinum, F. poae, F. sporotrichioides, F. culmorum* and *F. crookwellense* are capable of producing a class of compounds known as the trichothecenes. This large family of sesquiterpene epoxides are closely related and vary by the position and number of hydroxylations and substitutions of a basic chemical structure. The major trichothecene produced by *F. graminearum* is deoxynivalenol (DON) also known as vomitoxin for its ability to induce vomiting. These chemicals are potent eukaryotic protein synthesis inhibitors, toxic to both humans and animals, and other organisms such as plants.

Due to their toxicity, safety threshold values have been recommended for DON mycotoxin contamination in grain used for human food and animal feed. (Van Egmond, 1989, Food Addit Contam. 6:139–188; Underhill, CFIA Fact Sheet, Mycotoxins, 1996). The danger to livestock producers is that if livestock animals are fed contaminated grain they suffer severe health hazards, which include reduction of feed intake, reduced growth rate, reduced fertility, immunosuppression, diarrhea, vomiting and possible death. Some of these effects are directly observable and therefore measurable, such as weight loss, whereas other effects, such as immunosuppression, are more subtle and less quantifiable. In general, a reduction of 10 to 20% of the farrowing rate of swine combined with a 10 to 20% reduction in animal growth rates can cause an approximate 17 to 44% reduction in profit margin for hog producers. The effects of mycotoxins on poultry and cattle are less quantified since both of these species are less sensitive to DON contamination in their feed, and detailed economic threshold assessments have not been made.

During years of *Fusarium* epidemics, Canadian grain which is above the safety threshold of 2 ppm DON for human consumption must be downgraded to animal feed. If the grain contains more than 10 ppm DON, it is rendered unfit for animal feed and must be disposed of. Since many farmers use their own cereals for on-farm animal feed, and they may not be capable of assessing the level of mycotoxin contamination of the grain, a considerable amount of DON-contaminated feed is used. Thus it is important to minimize the level of trichothecenes in food stuffs, which can be accomplished by controlling the outbreaks of *Fusarium* species in cultivated cereal species.

Chemical treatment has been used in the past to control trichothecene biosynthesis. One such inhibitor is ancymidol, which has been described in U.S. Pat. No. 4,816,406. However, in the present environment, it is desirable to avoid chemical control, especially in food stuffs. Thus, there is a need for a method of controlling the outbreaks of Fusarium species, particularly *F. graminearum* by using non-chemical methods.

Trichothecenes have been shown to act as virulence factors in wheat head scab. This was demonstrated by inoculating wheat heads with trichothecene-nonproducing mutants of *F. graminearum* in which the first gene specific to the trichothecene biosynthetic pathway had been disrupted through genetic engineering (Desjardins et al., 1996, Mol. Plant-Micr. Int. 9:775–781). In two years of field trials, the trichothecene-nonproducing strains were less virulent than the trichothecene-producing progenitor or revertant strains, as measured by several disease parameters. Similar results have been obtained from the inoculation of field-grown corn with these trichothecene-producing and -nonproducing *Fusarium* strains (Harris, L. J. et al., 1999, Plant Diseases 83:954–960). Therefore, increasing the tolerance of wheat or corn to the effects of trichothecenes should lead to reduced disease.

SUMMARY OF THE INVENTION

The mode of action of all trichothecenes is related to their ability to bind the 60S ribosomal subunit and essentially inhibit protein synthesis. This is either accomplished by inhibiting the initiation of protein synthesis, the elongation of the growing peptide chain or termination of the peptide (Freinberg and McLaughlin, 1989, Biochemical mechanism of action of trichothecene mycotoxins, p27, In: Trichothocene Mycotoxicosis: Pathophysiologic Effects Vol 1 CRC Press, Boca Raton Fla.). The effect of these toxins on protein synthesis is observed in a diverse array of eukaryotic cells such as yeast and mammalian cell lines. Each ribosome has apparently only one binding site for the toxin, and much research suggests that all of the trichothecenes compete for the same ribosomal binding site on ribosomal protein L3.

The *Saccharomyces cerevisiae* (yeast) mutant which was spontaneously isolated by Schindler et al. (1974, Nature, 248: 548–536) was shown to be capable of growth on the trichothecene drug trichodermin. This yeast line was demonstrated to have altered 60S ribosomal subunit function and when the gene responsible was cloned, it was found to code for the ribosomal protein L3, (RPL3) (Schultz and Friesen, 1983, J. Bacteriol. 155:8–14).

In one aspect of the present invention, information obtained by comparing the wild type yeast gene and the mutant yeast gene was used to modify the corresponding gene from rice *Oryza sativa*, a cereal plant species. Transgenic tobacco plants were then created, using the modified rice gene, and these plants demonstrated a higher tolerance to the trichothecene mycotoxins than wild type tobacco plants, or plants transformed with the wild-type rice gene. Transgenic maize embryogenic cultures containing the modified rice Rpl3 gene, also exhibited a higher tolerance to the trichothecene DON, compared to cultures containing the wild-type rice Rpl3 gene. Thus this modified rice gene can provide protection against trichothecene mycotoxins and therefore provide resistance to *Fusarium* infestation in another plant species.

Thus according to the present invention there is provided a modified nucleic acid, wherein a host transformed with said nucleic acid is resistant to trichothecene mycotoxins, wherein the wild type form of said gene encodes a ribosomal protein L3.

In one embodiment of this aspect of the invention the nucleic acid encoding the ribosomal protein L3 is from rice.

The present invention further provides a suitable cloning vector containing said modified ribosomal protein L3 gene.

In a further aspect of this invention, the sequence of the cloned rice gene, and the resulting protein were compared with corresponding genes and proteins from six different monocots to identify the presence of a conserved target sequence for introduction of modification sites to provide a modified gene wherein a host transformed with said gene has increased resistance to trichothecene mycotoxins.

In yet a further aspect of the invention there is provided a transformed plant, transformed with the modified nucleic acid, wherein said transformed plant has increased resistance to *Fusarium* infestation.

The present invention also includes the seed from the transformed plant, referred to above.

In yet another aspect of the present invention there is provided a method of increasing resistance to *Fusarium* infestation by transforming a suitable plant with a modified nucleic acid, wherein the plant transformed with said nucleic acid has increased resistance to trichothecene mycotoxins, and wherein the wild type form of said gene encodes a ribosomal protein L3.

In a further aspect of the present invention there is provided a method of using the modified gene of the invention as a selectable marker in transformation experiments.

BRIEF DESCRIPTION OF THE DRAWINGS

These and other features of the invention will become more apparent from the following description in which reference is made to the appended drawings wherein:

FIG. 1 shows a comparison of the wild-type yeast RPL3 amino acid sequence (RPL13PWT; SEQ ID No.: 1), the upper line, and the Trichodermin-resistant yeast sequence (SCRP 13 PRO; SEQ ID No.: 2), the lower line. The amino acid change W-255 to C-255 is shown. The accession number in GenBank for the mutant yeast gene is J01351.

FIG. 5A), or the modified version of Rpl3 (C4 cells; FIG. 5B). Cells were grown in medium containing either no toxin or 25 ppm DON.

FIGS. 7A–7H show the alignment of monocot Rpl3 cDNA clones. The consensus sequences are aligned beginning at the putative ATG translation initiation codon, with the exception of the oat sequence which is a partial sequence. The sequences are as follows: maize1=SEQ ID NO:7; maize2 =SEQ ID NO:8; sorghum1=SEQ ID NO: 11; sorghum2 =SEQ ID NO: 12; wheat=SEQ ID NO:13; barley= SEQ ID NO: 10; oat=SEQ ID NO:9; rice=SEQ ID NO: 19; and Consensus =SEQ ID NO:20.

FIGS. 8A–8B show the alignment of predicted monocot RPL3 proteins. Sites at which amino acid differences occur among RPL3 proteins of the six species are noted above the sequence with an asterisk. The sequences are as follows: maize=SEQ ID NO:14; sorghum=SEQ ID NO:15; wheat= SEQ ID NO:16; barley=SEQ ID NO:17: oat =SEQ ID NO:18: and rice=SEQ ID NO:3.

DETAILED DESCRIPTION OF INVENTION

Figure 2:
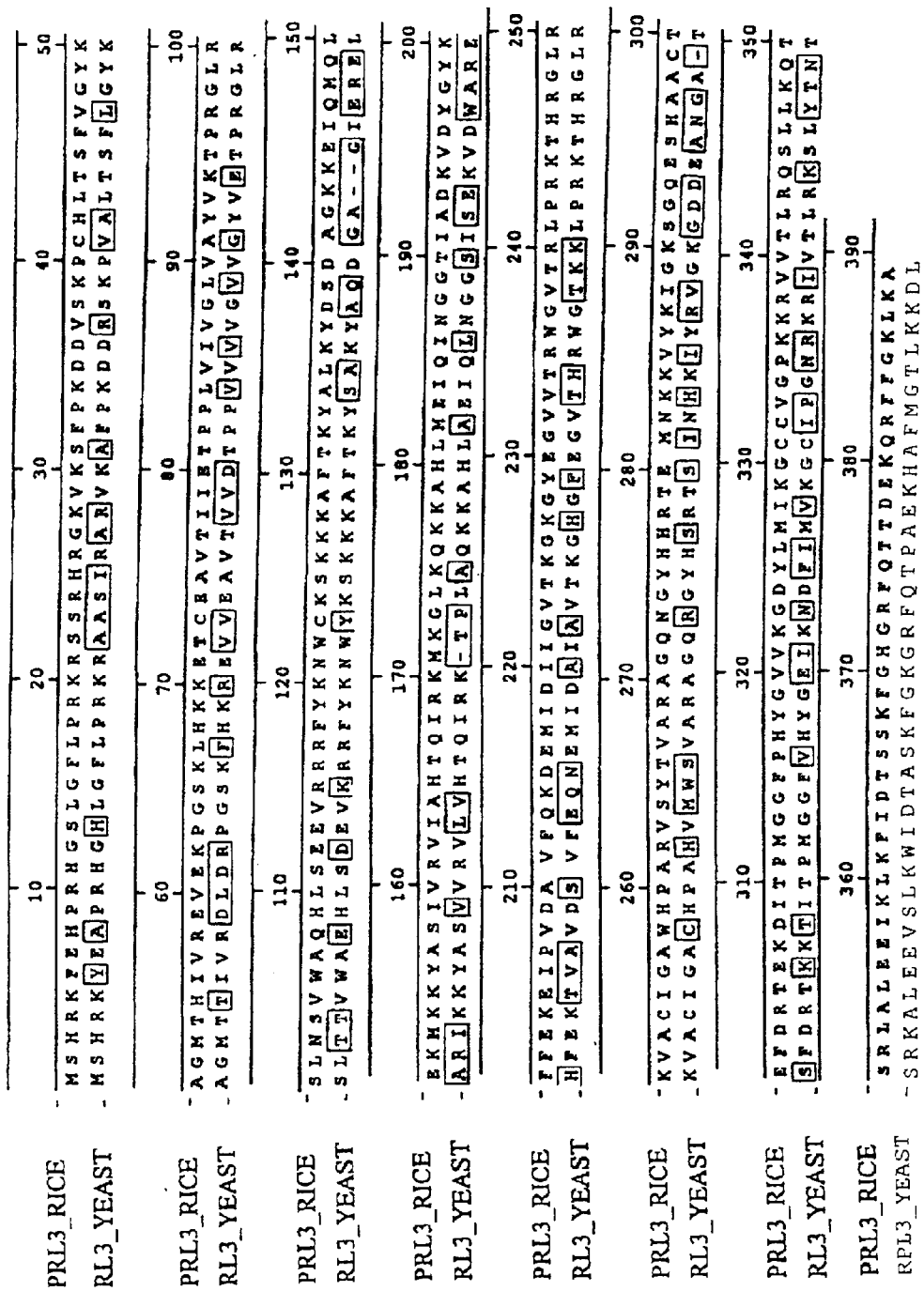
FIG. 2 shows the comparison of the rice RPL3 sequence (SEQ ID No.: 3), the upper line, and the trichodermin-resistant yeast sequence (SEQ ID No.: 2), the lower line. This comparison led to the predicted change of residue W258 (rice numbering) to C258, to create the mycotoxin tolerant rice gene Rpl3:c258. The accession number in GenBank for the rice gene is D12630.
Figure 3:
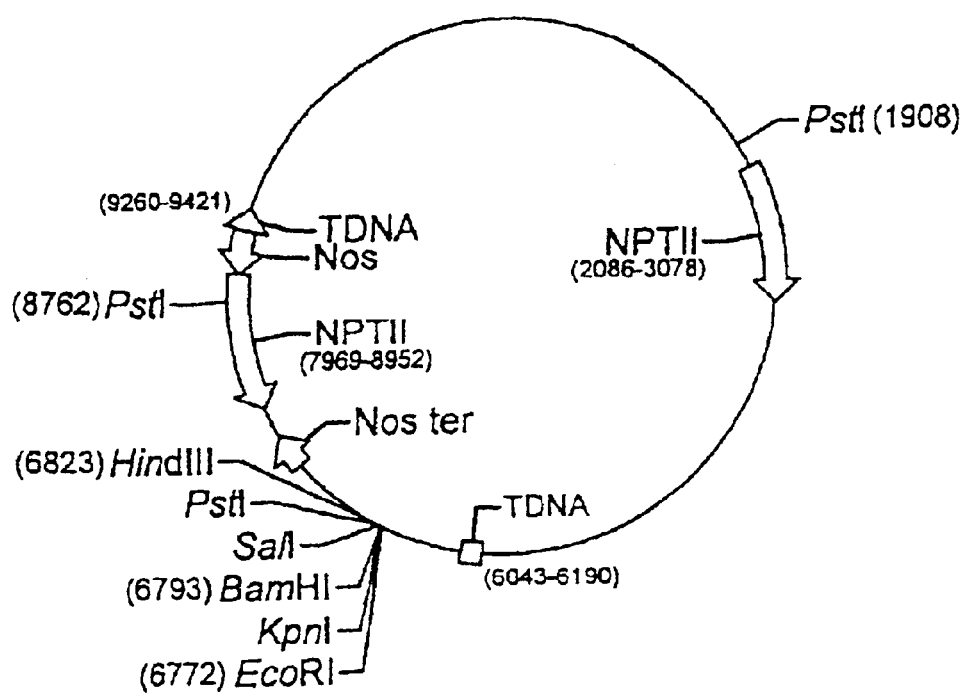
FIG. 3 shows the plasmid map of the *Agrobacterium tumefaciens* binary vector pBin 19 for plant transformation (Bevan, M. 1984, Nucleic Acids Research 12:8711–8721).
Figure 4:
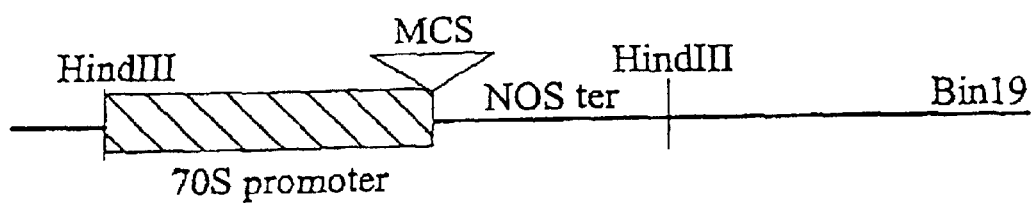
FIG. 4 shows the plasmid pCAMterX, which was used to clone the Rpl3 genes into the multiple cloning site (MCS). The Rpl3 genes were expressed under the direction of the Cauliflower mosaic virus (CAMV 35S promoter) arranged in tandem. (70S promoter).
Figure 5A:
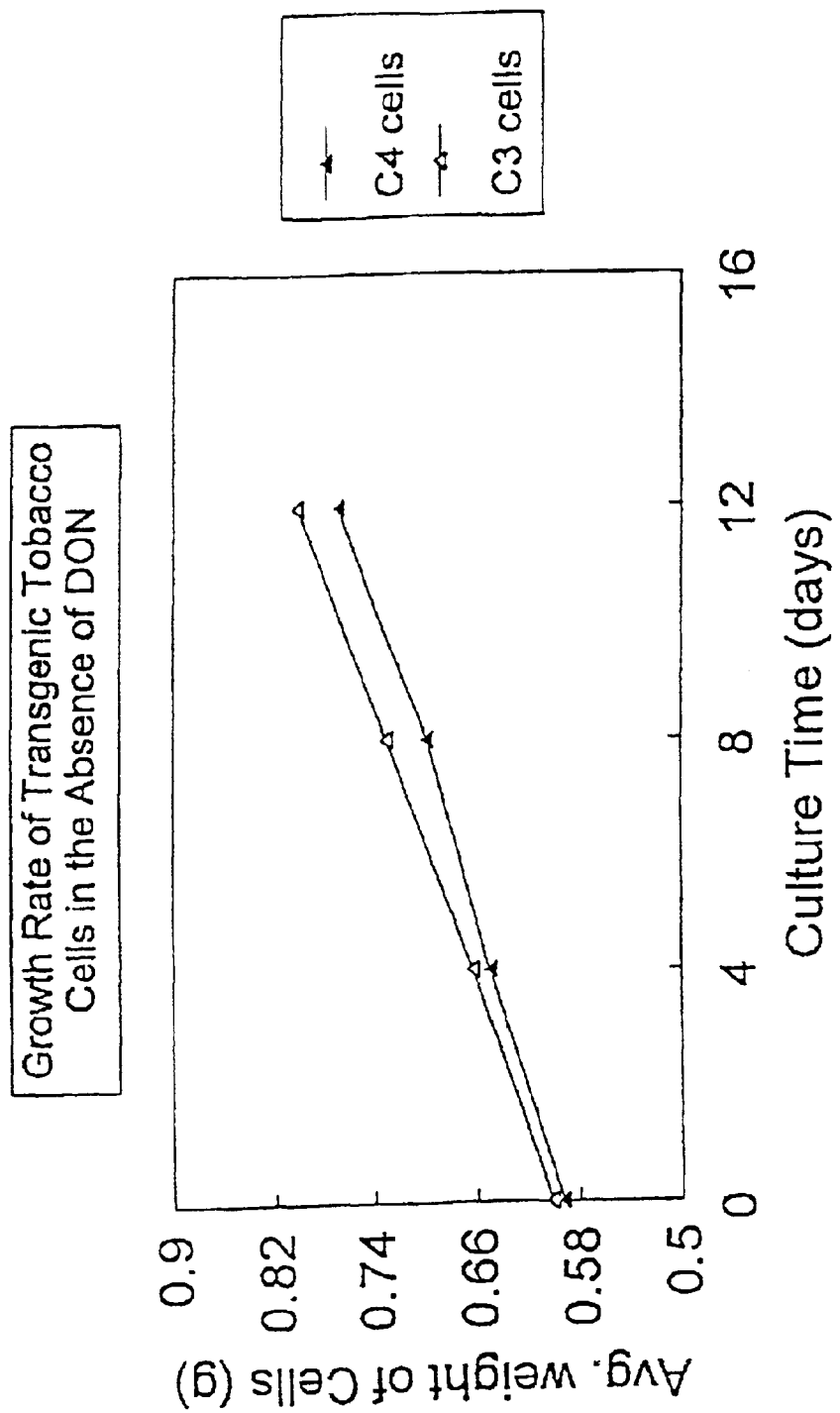
FIGS. 5A–5B show the growth rate of transgenic tobacco cells containing either the wild-type rice Rpl3 gene (C3 cells.
Figure 5B:
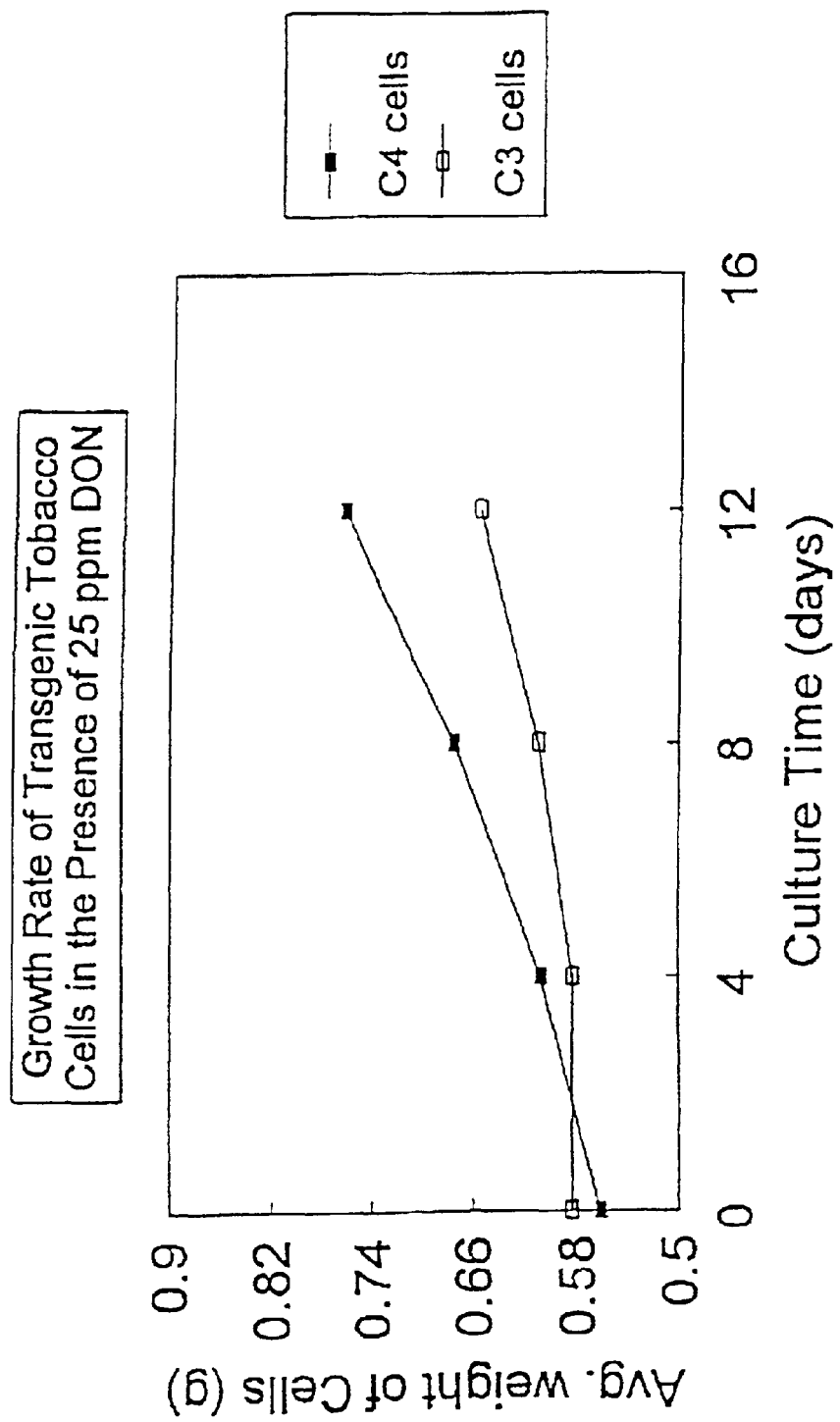
Figure 6:
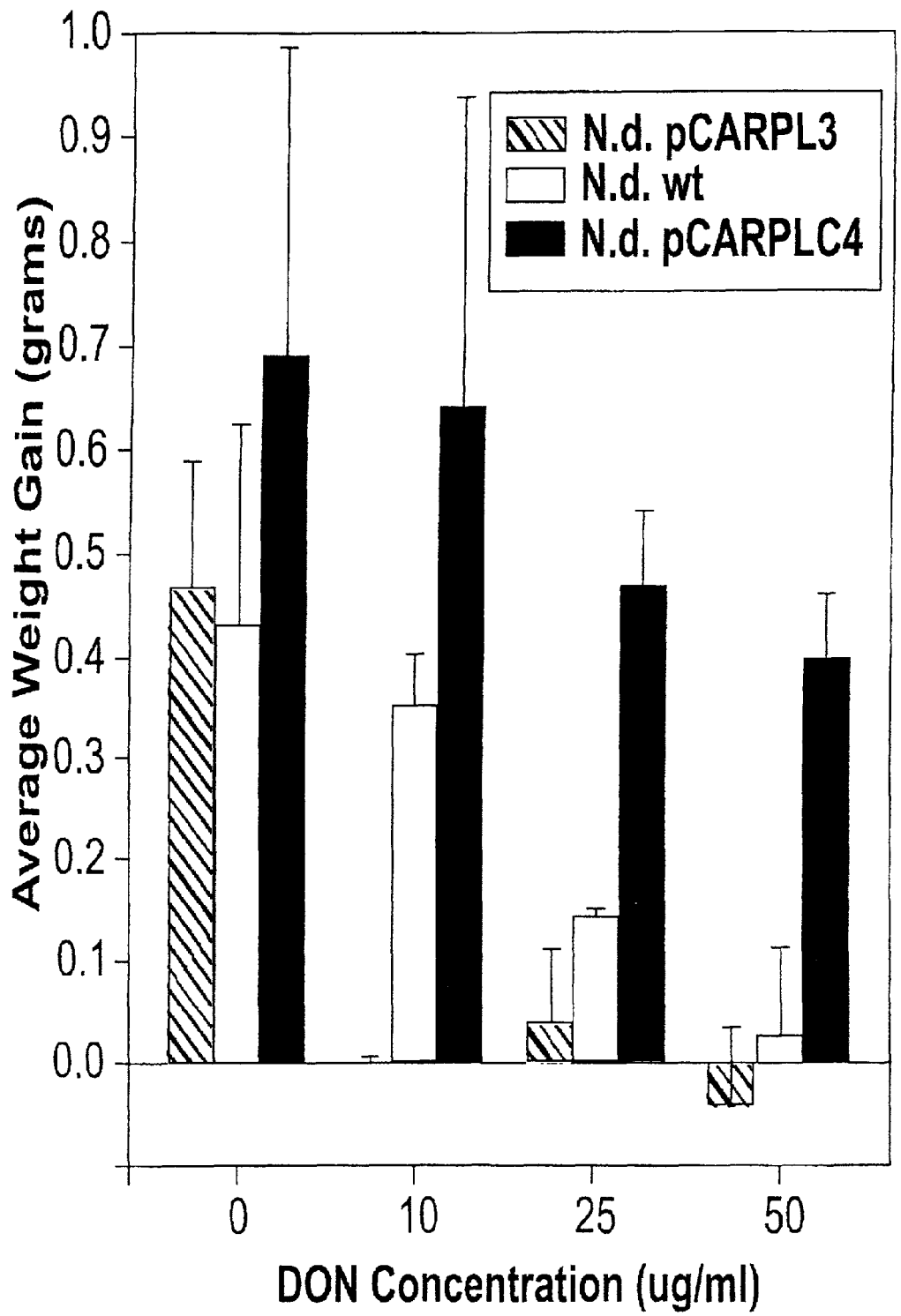
FIG. 6 shows the effect of DON on transgenic *N. debneyi* suspension cells cultured with various concentrations of DON. The weight gain of cells after 20 days in culture of a wild type non-transformed *N. debneyi* cell suspension (N.d.wt), and of a cell line established from a transgenic line expressing the wild-type rice Rpl3 gene (N.d.pCARPL3) were inhibited by increasing DON concentrations from 10 to 50 µg/ml in the medium. Cells of transgenic line expressing the rice Rpl3c:258 (N.dpCARPLC4) were not inhibited as much. Bars represent standard errors, one plant line per genotype was used, and the data is based upon three replicates.

According to the present invention there is provided a modified Rpl3 gene, whose gene product provides resistance to trichothecene mycotoxins. Previous work has shown that the trichothecenes bind to a single site on the eukaryotic 60S ribosome. A spontaneous mutant from the yeast *S. cerevisiae*, which is resistant to the trichothecene drug, trichodermin, has been identified. The corresponding wild-type gene was identified and the nature of the mutant gene was found to result from a single amino acid change at position 255 of the proposed RPL3 protein (FIG. 1).

This mutant represents only one example of a number of possible mutants of the same gene which would result in tolerance of the drug trichothecene trichodermin. Thus, the present invention is directed to a modified Rpl3 gene, wherein said modified gene provides resistance to the trichothecenes.

Not wanting to be bound by any particular theory, it is believed that the mycotoxin binds to the wild type protein but not to the mutant gene product. Thus the modified Rpl3 gene of the present invention would still have to allow the function of the peptidyl transferase in the ribosomal complex, but it would be modified to a sufficient extent to reduce the mycotoxin binding capabilities. If the mycotoxin has a reduced effect, the plant is more able to defend itself against the fungus and thus reduce the incidence of disease.

In one embodiment of this aspect of the invention the gene encoding the RPL3 protein is from a plant. In one example of this embodiment, the corresponding rice Rpl3 gene was identified and modified to reflect the modification in the yeast mutant gene. The resulting Rpl3 gene also provided resistance to the trichothecenes. A plant source of the Rpl3 gene was chosen in place of the yeast gene, as it was anticipated that the plant gene would have an improved expression in a plant host, than would the yeast gene.

Although the rice Rpl3 gene was used as an example other suitable plant genes could also have been used. Suitable examples include: the corresponding gene from *Arabidopsis thaliana* and monocotyledonous sources, for example barley, oats, sorghum, wheat and corn.

The area of modification in the yeast gene is in a highly conserved area. Shown below in Table 1 is the amino acid homology which occurs around this critical part of the protein, in plants, rats, mice, humans, yeast, *C. elegans* and *Escherichia coli*. Any of these could be used as source material for the Rpl3 gene. In each case the amino acid sequence would be aligned with the mutant yeast gene and the corresponding mutation made in the corresponding Rpl3 gene. As the entire area between the amino acid residue 240 and 263, based on the amino acid numbering in rice, is highly conserved, it is considered part of the present invention to modify any of the amino acids within this region to obtain a modified gene sequence. The modification could include substitutions or short length deletions, additions or inversions. As noted previously the modified gene product must continue to allow the function of the ribosomal protein and peptidyl transferase activity, but have reduced binding capabilities to the mycotoxin.

Figure 7A:
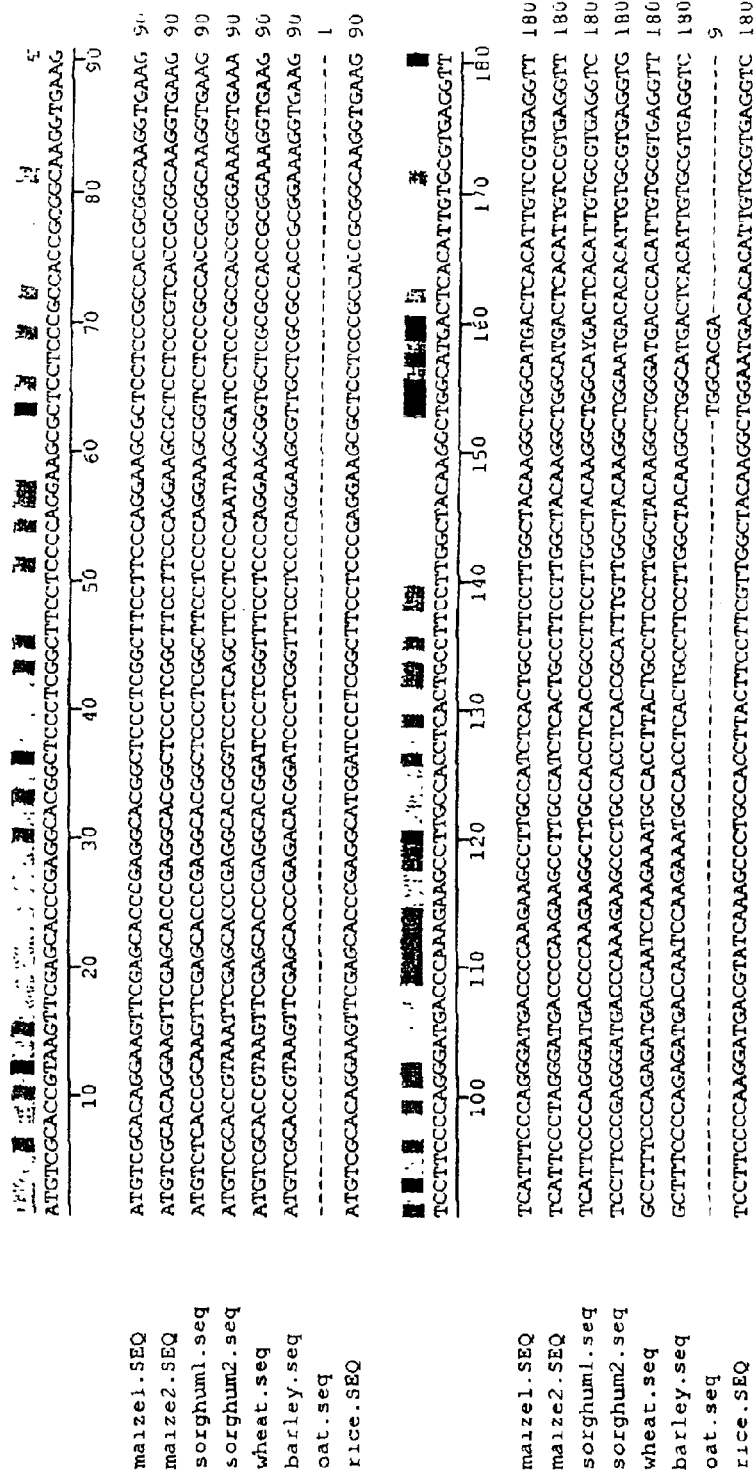
Figure 7G:
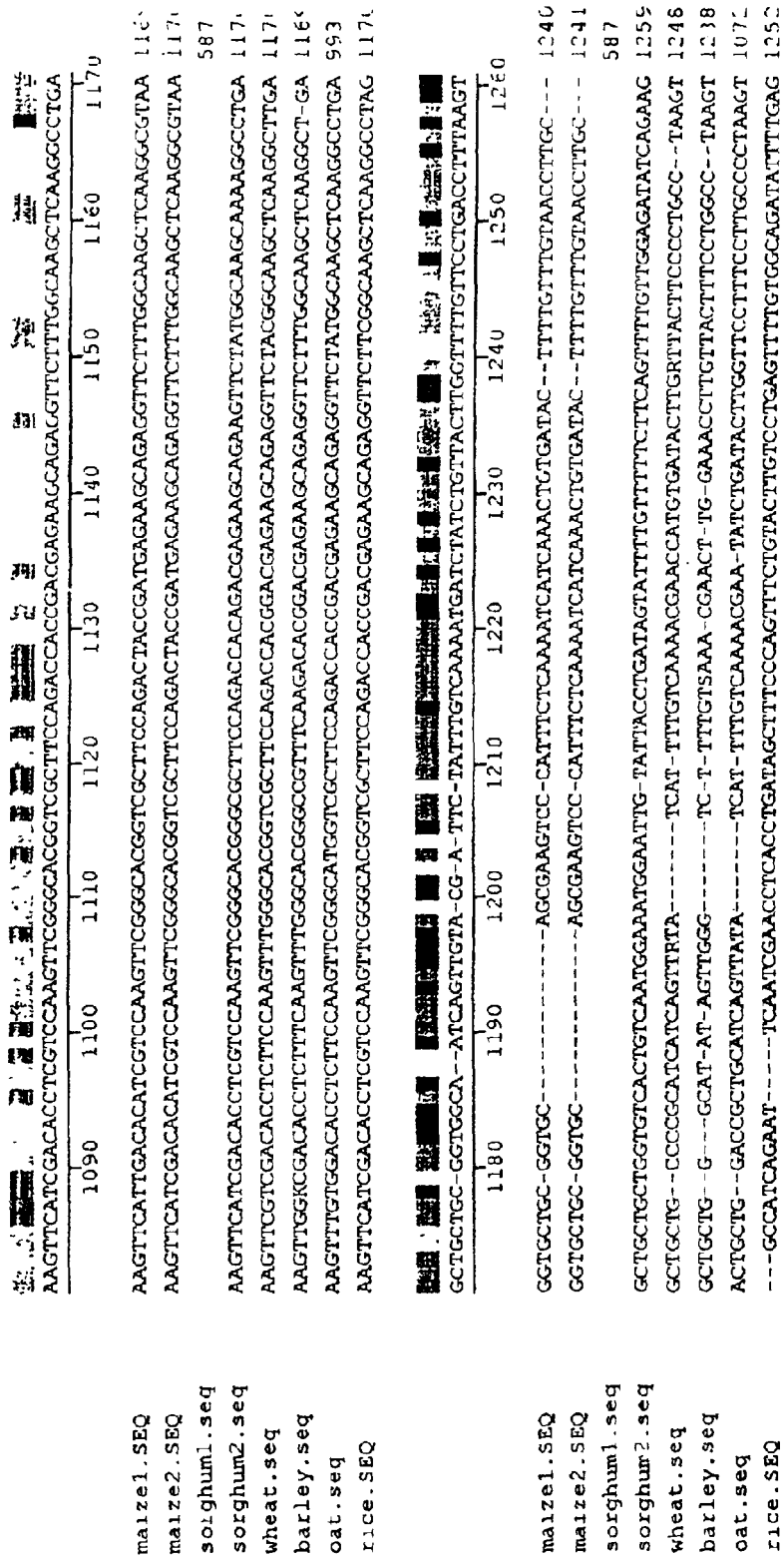
Figure 9:
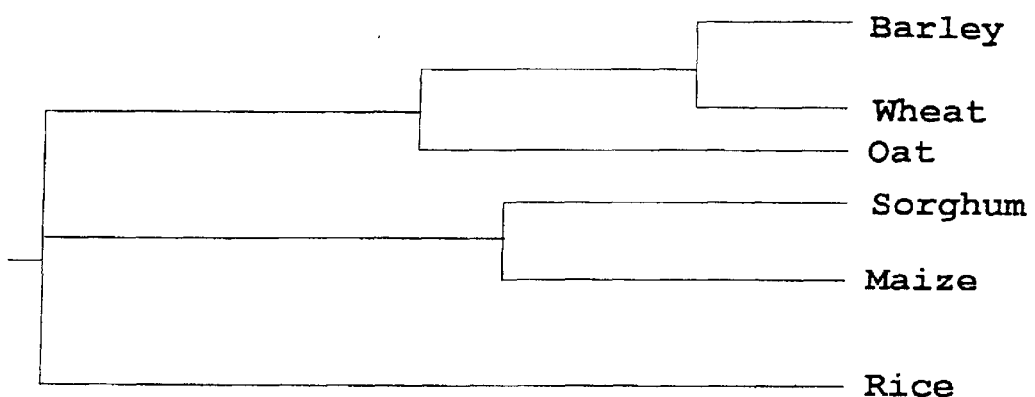
FIG. 9 shows the phylogenetic tree of monocot RPL3 proteins.

As shown in FIGS. 7 and 8, the nucleic acid and protein sequences are highly conserved between a number of monocot Rpl3 genes. An alignment of the monocot proteins reveals that these proteins are completely conserved between amino acid 209 and 284. The overall amino acid sequence identity is at least 92.5%. Thus, the strategy applied in the following example in rice can be applied to other plant genes, including genes from the family of monocots.

TABLE 1

Comparison of the Sequence of Various Ribosomal protein L3 Between Residues 240 and 263

Amino Acid Sequence

| | Residue 240 | | | | | | | | | | | | | | | | | | 258 | | | | | 263 |
|---|---|---|---|---|---|---|---|---|---|---|---|---|---|---|---|---|---|---|---|---|---|---|---|---|
| Rice | R | | | | | | | | | | | | | | | | | | | | | | | R |
| Arabidopsis 1 | R | | | | | | | | | | | | | | | | | | | | | | | R |
| Arabidopsis 2 | R | | | | | | | | | | | | | | | | | | | | | | | R |
| YEAST (wt) | K | L | P | R | K | T | H | R | G | L | R | K | V | A | C | I | G | A | W | H | P | A | H | V |
| Bovine | | | | | | | | | | | | | | | | | | | | | | | | R |
| Rat | | | | | | | | | | | | | | | | | | | | | | | | R |
| Mouse | | | | | | | | | | | | | | | | | | | | | | | | R |
| Human 1 | | | | | | | | | | | | | | | | | | | | | | | | R |
| Human 2 | | | | | | | | | | | | | | | | | | | | | | | | R |
| Human 3 | | | | | | | | | | | | | | | | | | | | | | | | R |

Bars represent amino acids identical to the wildtype yeast Rpl3 sequence.

The present invention further provides a suitable cloning vector containing said modified Rpl3 gene. Any cloning vector can be used. The cloning vector chosen will of course reflect the host in which the final transformation will be made.

Suitable plant cloning vectors can include: the binary Agrobacterium vectors, such as Bin 19 (Bevan, M., 1984, Nucleic Acids Research 12:8711–8721) and the vectors used for microprojectile bombardment of monocots.

For the transformation of plants, the cloning vector can further comprise a 3' untranslated region. A 3' untranslated region refers to that portion of a gene comprising a DNA segment that contains a polyadenylation signal and any other regulatory signals capable of effecting mRNA A processing or gene expression. The polyadenylation signal is usually characterized by directing the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the modified Rpl3 gene of the present construct can be used for expression in plants, without any additional region.

The vectors of the present invention can also contain a suitable promoter. In the plant transformation examples of the present invention any strong constitutive, inducible or tissue-specific promoter will be suitable. Suitable examples include but are not limited to the Cauliflower mosaic virus (CAMV 35S). It can be used alone or together with other plant promoters.

The cloning vector of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the vector of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

Also considered part of this invention are transgenic plants containing the modified Rpl3 gene of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The vector constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421–463 (1988); and Geierson and Corey, *Plant Molecular Biology*, 2d Ed. (1988).

Suitable plant hosts include but are not limited to corn, barley, wheat, rice, rye, oats and millet. Since only a single base pair of DNA in the wild type Rpl3 gene needs to be changed, the science introducing the modified gene using a cloning vector and traditional plant transformation techniques, the gene modification can be accomplished using a technique known as chimeraplasty.

Chimeraplaty employs a chimeric DNA/RNA molecule which is introduced into cells and causes the homologous endogenous gene to be precisely modified. The modification is made at the gene's normal position in the genome and the introduced DNA/RNA molecule is not expected to be integrated so that problems often associated with introducing transgenes (eg. Transgene silencing, positon effects) are avoided. This technique has been used in gene repair in mammalian cells, for example sickle cell anemia (Cole-Strauss et al., 1996, Correction of the mutation responsible for sickle cell anemia by an RNA/DNA oligonucleotide, Science 273:1386–1389), and for gene activation and modification in plant cells (Beetham, P., Kipp, P., Sawycky, X., Arntzen, C., and May, G., 1999, A tool for plant genomics: chimeric RNA/DNA oligonucleotides cause in vivo gene-specific mutations, Proc. Natl. Acad. Sci. USA 96:8774–8778; and Zhu, T, 1999, Targeted manipulation of maize genes in vivo using chimeric RNA/DNA oligonucleotides, Proc. Natl. Acad. Sci. USA. 96:8768–8773.). By a similar approach, it would be possible to modify the endogenous genes of maize, wheat, rice, or any other *Fusarium*-susceptible cereal species such that their endogenous Rpl3 genes contain the modification described in the present invention. According to our characterization of the Rpl3 gene family in maize, it has been determined that there are 3–4 functional copies of the Rpl3 gene in some inbred lines. Since the modified rice Rpl3:c258 gene behaved in a dominant fashion in transgenic plants, the endogenous gene(s) modified by chimeraplasty should be sufficient to confer DON tolerance upon susceptible plants. Thus, for the purposes of the present invention, when transgenic plants are discussed or claimed, it is intended that the claim covers plants modified by any method described in this application or known to persons of ordinary skill in the art.

When specific sequences are referred to in the present invention, it is understood that these sequences include within their scope sequences that are "substantially homologous" to said specific sequences. Sequences are "substantially homologous" when at least about 70%, preferably at least about 80% and most preferably at least about 90 to 95% of the nucleotides match over a defined length of the molecule. Sequences that are "substantially homologous" include any substitution, deletion, or addition within the sequence. DNA sequences that are substantially homologous can be identified in Southern hybridization experiments, for example under stringent hybridization conditions (see Maniatis et al., in Molecular Cloning (A Laboratory Manual), Cold Spring Harbor Laboratory (1982) p 387 to 389).

The specific sequences, referred to in the present invention, also include sequences which are "functionally equivalent" to said specific sequences. In the present invention functionally equivalent sequences refer to sequences which although not identical to the specific sequences provide the same or substantially the same function. DNA sequences that are functionally equivalent include any substitution, deletion or addition within the sequence. With reference to the present invention functionally equivalent sequences will provide resistance to the trichothecenes. As has been described before, the modified gene of the present invention must still allow ribosomal L3 activity but have reduced binding capabilities for the mycotoxin.

Thus, a further aspect of the invention is a transformed plant, transformed with the modified Rpl3 gene, wherein the transformed plant has increased resistance to *Fusarium* infestation.

In yet another aspect of the present invention there is provided a method of conferring resistance to *Fusarium* infestation comprising the steps of: providing a modified gene or gene fragment, wherein the wild type form of said gene encodes an RPL3 protein; and transforming a suitable plant with said modified gene.

Another aspect of the present invention is the use of the modified gene as a selectable marker in transformation experiments. Selectable marker genes such as the neomycin phosphotransferase npt II from bacterial transposons, or the hygromycin phosphotransferase hpt, or the mammalian dihydrofolate reductase gene dhfr have been successfully employed in many plant systems (Sproule et al., 1991, Theor. Appl. Genet, 82: 450–456; Dijak et al., 1991, Plant Cell Tissue and Organ Culture 25: 189–197). These genes have permitted the use of the antibiotics kanamycin, hygromycin and methotrexate respectively, in the selection of transgenic plants and at the protoplast level for the selection of somatic hybrids. Alternatively, selection strategies have utility in science for the performance of multiple transformations, that is the repeated transformation of one plant with several different genes. To effect this, new and effective selective agents are desirable. Novel selection strategies based on genes which detoxify compounds other than antibiotics are also useful in cases where the use of antibiotics degrading or detoxification genes are not permitted or wanted in the transgenic organism. Under these cases it would be desirable to have a gene which confers a useful phenotype (disease resistance) as a selectable marker.

According to the present invention plant or animal cells that are exposed to DON are unable to proliferate in the presence of this toxin. Cell lines transformed with the modified gene of the present invention are more resistant to DON and will grow in a medium containing from 0.1 ppm to 50 ppm of DON. In one example of the present invention 0.5 to 10 ppm DON can be used in a selection medium. Thus the modified gene can be used as a selectable marker in transformation experiments, wherein only the cell lines that have become transformed with a vector containing the modified gene will grow in a selection medium containing DON. Thus, for example, the modified gene of the present invention could be used as a selectable marker in plant or animal transformation experiments in the same manner as genes providing resistance to gentamycin, hygromycin, kanamycin, and the like are presently used.

While this invention is described in detail with particular reference to preferred embodiments thereof, said embodiments are offered to illustrate but not limit the invention.

EXAMPLES

Example 1

Modification of the Rice Rpl3 Gene

The wildtype DNA sequence of the yeast Tcm1 gene was obtained from M. Bolotin-Fukuhara of the Yeast Genome Sequencing Project. Upon comparison of the Tcm1 DNA sequence with the mutant tcm1 sequence, a single base pair change was observed. This change converts a tryptophan (Tcm1) to a cysteine (tcm1) at residue 255 (based on the yeast numbering system) in the proposed RPL3 protein (FIG. 1).

In this example of the present invention, the corresponding rice Rpl3 gene was converted to a form resembling that of the yeast trichodermin resistance gene (tcm1).

A rice Rpl3 cDNA, containing a 21 bp 5' non-coding region, a 1170 bp coding region, and a 177 bp 3' non-coding region (including a partial polyA tail), was kindly provided by Dr. A. Kato (Hokkaido University, Japan). The cDNA (originally named T82, renamed pOSRPL3) was received as a 1368 bp insert in the SmaI/EcoRI site of pIBI31. This rice cDNA was randomly cloned from rice suspension culture cells (Uchimaya et al., 1992, Plant J. 2:1005–1009). A database search had revealed sequence homology with numerous ribosomal protein L3 genes (Nishi et al., 1993, Biochimica et Biophysica Acta 1216:110–112).

The proposed proteins coded for by the rice Rpl3 and the yeast Tcm1 genes share 65% amino acid identity. The tryptophan-to-cysteine change observed between the yeast gene alleles lies within a region well conserved in the rice gene; 17 amino acids 5', the tryptophan residue itself, and 3 amino acids 3' of the tryptophan are completely conserved between rice and yeast (FIG. 2 and Table 1).

Thus, site specific mutagenesis was employed to modify the rice Rpl3 cDNA to resemble the yeast tcm1 gene at the critical site.

pOSRPL3 was digested with XbaI and NaeI, yielding a 1722 bp fragment encompassing the Rpl3 cDNA. This fragment was subcloned into the XbaI/HpaI site of the pALTER-EX1 vector (Promega) and named pALTRPL3. An 18 bp oligomer (5'-GGCTGGATGGCAGGCACC; SEQ ID No.: 4) was used to produce the desired mutation with the aid of the Altered Sites kit (Promega). DNA sequencing confirmed the mutagenesis was successful and the resultant clone was named pALTRPLC4.

Example 2

Vector Construction and Transformation

The upstream XbaI site and an EcoRI site 8 bp past the rice Rpl3 TAG stop codon were used to subclone either the unmodified or modified form of the gene into pCAMterX. pCAMterX is derived from pBIN19 (Bevan, M., 1984, Nucleic Acids Research, 12:8711–8721; FIG. 3) and has had a 70S CaMV promoter, multiple cloning site, and nos 3' terminator added. Plasmids containing the unmodified and modified Rpl3 genes subcloned into pCAMterX (FIG. 4) were named pCARPL3 and pCARPLC4, respectively. These two clones were transformed into Agrobacterium strain GV3101/pmp90 which was subsequently used to transform *Nicotiana tabacum* cultivar Delgold and *N. debneyi*. Transformed lines of *N. tabacum* and *N. debneyi* were selected on regeneration medium (Sproule et al. 1991, Theor. Appl. Genet. 82:450–456) containing 150 $\mu$g/ml kanamycin.

Example 3

Tobacco Transformation

The vectors containing the unmodified and modified Rpl3 genes (pCARPL3 and pCARPLC4 respectively) were used to transform wild-type tobacco (*Nicotiana tobacum*) and a wild, diploid species *N. debneyi*. Both genes were transferred into these tobacco species at equal frequencies which suggests that neither rice gene had a negative effect on growth, regeneration, or seed production. For example, 70 and 63 independent transgenic lines of *N. debneyi* were recovered for the pCARPL3 and pCARPLC4 genes, respectively. Southern hybridization data and progeny testing of seeds from these transgenic plants was used to verify that the plants chosen for detailed analysis had single copy insertions.

Example 4

Protoplast Isolation and Culture

Seed harvested from transgenic *Nicotiana tabacum* and *N. debneyi* were surface sterilized in 70% Javex solution for 2–3 min followed by 5 rinses in sterile distilled water. They were planted (20 seeds per 60×20 mm petri plate) onto the surface of agar-solidified B5 medium (Gibco) containing 150 $\mu$g/ml kanamycin and maintained at 25° C. in 16 hr day length of 100 uE m sec. Those seedlings which germinated and remained green following two weeks of selection were transferred to fresh petri plates containing half strength MS medium (Gibco) lacking kanamycin. These plants were maintained inside sterile Magenta containers in a growth room at 25° C. in 16 hr day length of 100 uE m sec.

The protoplast isolation from leaf mesophyll cells was as described by Sproule et al. (1991, Theor. Appl. Genet. 82:450–456). An enzyme solution of 1% (w/v) cellulase R-10 and macerozyme R-10 in 0.45M mannitol salt solution was filter sterilized and 20 ml was aliquoted to sterile 100×15 mm petri dishes. Five leaves of each donor plant were excised and floated abaxial side down over the enzyme solution. Petri dishes were sealed with parafilm, incubated in a humid box in a dark growth chamber at 28° C. for 17 hrs with gentle agitation. The liberated protoplasts were separated from tissue debris by filtration through a sterile 88um mesh nylon funnel. The protoplast-enzyme solution was aliquoted into round-bottom sterile glass test tubes and centrifuged at 900 rpm for 10 min. Isolated protoplasts were separated from cellular debris by flotation on the surface of 4 ml of sterile 0.6M sucrose solution with an overlay of 0.5 ml of SCM (0.45M sorbitol, 10 μg/ml $CaCl_2.2H_2O$, 5 μg/ml MES morpholinoethane sulfonic acid; pH 5.8). Purified protoplasts were recovered from the SCM interface with sterile pipettes. Protoplasts were adjusted to a density of $5 \times 10^4$ cells/ml with a haemocytometer, in liquid NT medium (Nagata and Takebe, 1991, Planta 99: 12–20) containing 0.4M glucose as osmoticum.

A stock solution of DON, produced according to the method of Greenhalgh et al. (1986, J. Agric. Food Chem. 34: 98–102) was used to adjust the concentration of DON toxin in some protoplast cultures to either 0, 0.1, 1.0, 5.0, or 10.0 ppm. All protoplast cultures were 2 ml of liquid, incubated in sterile 60×15 mm petri dishes at 28° C. in darkness. After one week of culture, the osmotic concentration of the medium was adjusted by the addition of 0.5 ml of NT medium containing 0.3M glucose, and the protoplast cultures were moved to low light (10 uE m sec) at 25° C.

The wild-type plants were shown to be susceptible to DON at 0.5 to 10 ppm in culture medium. The effect of DON on these protoplasts was to reduce the ability of protoplasts to reform cell walls, reduce the division frequency (mitotic index of the cells), and reduce the plating efficiency (number of micro colonies formed) of protoplasts relative to those cultured in the absence of DON.

The viability of protoplasts of the genotype Rpl3:c258 (C4 lines) were not significantly affected by culture for 20 days in medium supplemented with 0.5 to 25 ppm DON. Whereas the viability of protoplasts containing Rpl3:c258 in the absence of DON was about 65%, it was 56% when these protoplasts were cultured in the presence of 25 ppm DON. Protoplasts from wild-type tobacco plants when cultured in NT medium supplemented with 25 ppm DON exhibited 18% viability while those from transgenic plants with the rice Rpl3 gene (C3 lines) had less than 10% viability. This effect on leaf mesophyll protoplasts was not due to the general effect of each genotype, since in the absence of DON each line had viabilities in NT medium ranging from 58% to 66%. The pronounced differences between genotypes became apparent when protoplasts were cultured in the presence of the mycotoxin DON.

Protoplasts were also cultured over 2 ml agarose underlayers (0.4% w/v) inside sterile 60×15 mm petri dishes. The agarose underlayers contained either 0, 0.1, 1.0, 10, or 25 ppm DON.

Protoplasts in these cultures were suspended in liquid NT medium at a density of $1\times10^5$ per ml and cultured as in Sproule et al. (1991, Theor. Appl. Genet. 82:450–456).

When protoplasts were cultured on medium supplemented with DON, noticeable differences were observed in micro colony formation (cell colonies from isolated protoplasts). Colonies from protoplasts containing Rpl3 did not often develop into calli, and therefore were not transferred to regeneration medium whereas micro colonies containing Rpl3:c258 were capable of transfer to regeneration medium.

Example 5

Cell Suspension Cultures

Cell suspension cultures from primary transgenic or wild-type tobacco plants were initiated from leaf callus cultures. Two grams of callus were ground in a sterile blender, and the homogenized tissue was used to inoculate 33 ml of liquid MS medium containing 2 $\mu$g/ml 2,4-D in a sterile 125 ml erlenmeyer flask. Cell suspensions were maintained on an orbital shaker at 150 rpm under a 16 hr day length at 25° C. with a weekly sub-culture of 5–10 ml of cells into 33 ml of fresh medium.

DON growth assays

Growth measurements of cell suspensions of *N. debneyi* and *N. tabacum* (Rpl3 and Rpl3:c258) were taken after the cultures had equilibrated in growth conditions for at least 12 weeks. The measure of weight gain was determined by plating 1 ml of finely filtered cell suspensions on sterile Millipore millicell HA filters (0.45 um×30 mm diameter) inside sterile 20×60 mm petri dishes containing 2 ml of liquid MS medium with 2 $\mu$g/ml 2,4-D, supplemented with either 0, 10, 25 or 50 $\mu$g/ml DON. At 5 day intervals the fresh weight of each filter unit was determined under aseptic conditions and then the cells were re-cultured on the same medium with fresh DON added. Cells of both transgenic genotypes were equally capable of growth when transferred to agar-solidified medium supplemented with kanamycin, indicating the stability and presence of the transgenes in these cell cultures. Leaf explants of all genotypes were evaluated for the ability to regenerate shoots on shoot regeneration medium (MS medium containing 3% sucrose, 1 $\mu$g/ml benzylaminopurine, 0.1 g/ml naphthalene acetic acid, 0.8% agar) supplemented with either 150 $\mu$g/ml kanamycin or 0, 5, Or 10 $\mu$g/ml DON.

DON at 25 ppm was sufficient to inhibit the packed cell volume and the gresh weight fain of cell suspensions of pCARPL3 plants. These levels of DON had a less serious impact on packed cell volume, or cell fresh weight gain of cultures of pCARPL3 (FIGS. 5 and 6).

DON was also capable of inhibiting the formation of callus and shoots on leaf explants cultured in vitro from leaves of wild-type and pCAPRL3 plants, whereas explants from pCARPLC4 plants were capable of shoot regeneration in the presence of DON.

Example 6

Monocot Transformation

The unmodified Rpl3 and modified Rpl3:c258 genes were cloned into a monocot expression vector under the control of the rice actin promoter and intron elements (pCOR13 provided by Prof. Ray Wu, University of Cornell, N.Y.) to provide pActRPL3 and pActRPLC4, respectively, for constitutive expression in monocots. These constructs were introduced by particle bombardment into cells of embryogenic maize tissue cultures derived from immature F1 embryos of maize A188xB73. To obtain transgenic lines, each construct was co-bombarded with a selectable herbicide resistant gene-pAHC25 containing the Bar gene (provided by Dr. Peter Quail, UC Berkeley Calif.) and phosphinothricin resistant cultures were established. Southern blot analysis of these cultures identified lines with RPL3 and RPLC4 integrated into high molecular weight maize DNA.

Example 7

Transgenic Monocot Cultures

Numerous researchers have shown growth inhibition of various monocot tissues by DON.

Bruins et al. (1993, Plant Sci. 94:195–206) demonstrated that DON reduces growth of wheat anther-derived callus tissue. DON concentrations of 10 μg/ml were sufficient to significantly inhibit growth of mature maize embryos (McLean, 1996, Mycopathologia 132:173–183). A dose of 100 μg/ml DON was lethal to most wheat calli (Menke-Milczarek and Jimny, 1991, Mycotox. Res. 7:146–149).

One line of each of RPL3 and RPLC4 was chosen which exhibited a low copy number of the transgene by Southern analysis. Calli from these two lines had undergone identical selection regimes and were of the same age. These two lines were tested for their ability to grow on media containing 0 to 25 μg/ml DON. Callus growth on media containing DON showed that the RPLC4 line was substantially more tolerant to mycotoxin. RPL3 growth was reduced to 15% of the control by 5 μg/ml DON whereas the RPLC4 line was reduced to only 63% of the control value by the same level of DON (Table 2). To reduce growth of the RPLC4 line to 15% of control values required 50 μg/ml DON. This represents a 10-fold increase in tolerance to DON by the RPLC4 callus.

TABLE 2

Effect of DON on growth of maize embryogenic cultures (A188xB73) transformed with pActRPL3 and pActRPLC4
Initial dry wt.-RPL3 = 1.4 mg, RPLC4 = 1.5 mg. Final dry weight after 3 weeks culture in the dark at 25° C. 12 explants/treatment

| | DON μg/ml | | | | |
|---|---|---|---|---|---|
| | 0 | 5 | 10 | 25 | 50 |
| pActRPL3 | 31.1 | 4.9 | 3.3 | 3.2 | 2.2 |
| pActRPLC4 | 29.8 | 18.7 | 13.1 | 7.0 | 4.4 |

These plants were selfcrossed to establish uniform homozygous lines and are being increased in the field for *Fusarium* resistance studies.

Example 8

Selection of a Target Sequence for Introduction of Additional Modifications to the Rpl3 Gene A number of monocot Rpl3 cDNA clones have been cloned and sequenced or retrieved from databases and compiled. Including the previously isolated rice cDNA sequence, we have compared the Rpl3 cDNA sequences from 6 different monocots. Maize, barley, wheat, rice and oats are all susceptible to *Fusarium* species producing trichothecene mycotoxtins. An alignment of monocot RPL3 proteins reveals that these proteins are completely conserved between amino acid 209 and 284 (the modified site conferring DON tolerance is at position 258) (FIG. 8). The overall amino acid sequence identity is at least 92.5%. These sequences demonstrate the high sequence identity between monocot Rpl3 genes and the capability of applying our modified Rpl3 gene strategy to confer trichothecene tolerance to all monocots.

Maize (*Zea mays*)

Total RNA was isolated either from silk or aleurone tissue from maize inbred CO325 (containing some gibberella ear rot kernel resistance) using the TRIzol reagent (Gibco/BRL), precipitated and resuspended in water. Total RNA was reverse-transcribed using a 3'-Rpl3-specific primer (CRPL31104L: 5'-AAGCGACCGTGCCCGAAC)(SEQ ID No.: 5). The Rpl3-specific sequence was amplified using primers CRPL31104L and CRPL33U (5'-GTCGCACAGGAAGTTCGA)(SEQ ID No.: 6) using the Expand High Fidelity PCR System (Boehringer Mannheim). PCR products were ligated into the pGEM-Teasy vector (Promega) overnight at 4° C. and transformed into electro-competent DH5α cells. Sequencing was either performed manually or by a commercial Licor sequencing service and sequences were compiled and analysed in a Lasergene DNAStar DNA analysis program. The sequenced RT-PCR clones fell into two classes of cDNA, represented by maize1 (SEQ ID No.: 7) and maize2 (SEQ ID No.: 8) in FIG. 7.

The genomic copies of three Rpl3 gene members were also isolated from inbred CO325 (data not shown). A BglII digestion of CO325 genomic DNA yields five Rpl3-hybridizing bands at 5, 6, 14 (doublet), and >22 kb. Three of these bands (5, 6 and 14 kb) were cloned by screening size-fractionated genomic bacteriophage libraries, using either the λZAP or λDASHII vectors (Stratagene). The 5 kb and one of the 14 kb copies appear intact and functional by sequencing. The 6 kb sequence appears to be a pseudogene as the Rpl3-hybridizing sequences are fragmented by DNA insertions.

Oat (*Avena sativa*)

Using our corn Rpl3 cDNA sequence, we identified an oat EST (CDO9650) in the International Triticeae EST Cooperative (ITEC) database with Rpl3 homology. However, the EST sequence did not include the region which codes for the tryptophan located at position 258. We obtained the original CDO0650 clone (courtesy of M. Sorrells, Cornell Univ.) which contained a 1.05 kb insert in a Bluescript vector (pBS SK-). Sequencing of the CDO0650 clone yielded the sequence oat shown in FIG. 7 (SEQ ID No.: 9). This sequence starts within the Rpl3 coding region at amino acid 60.

Barley (*Hordeum vulgare*)

A search of the Genbank EST database with our maize Rpl3 cDNA sequence produced 4 barley ESTs with Rpl3 homology and a search of the ITEC database furnished 5 additional ESTs. Seven of these nine sequences were of sufficient quality to produce a consensus barley Rpl3 cDNA sequence shown in FIG. 7 (SEQ ID NO: 10) (contributing EST sequences: AW926013; AW982571; BE231076; BE231182; MCG009.F09R990625; MCG010.F12R990625; PSR6521).

Sorghum (*Sorghum bicolor*)

A search of the Genbank EST database with our maize Rpl3 cDNA sequence produced 6 sorghum ESTs (accession nos. AW286798, AW677029, AW677280, AW677380, AW745612, AW924185) with Rpl3 homology. These 6 sequences were separated into two classes by sequence identity and compiled to produce two consensus sorghum Rpl3 cDNA sequences, sorghum1 (SEQ ID No.: 11) and sorghum2 (SEQ ID No.: 12) in FIG. 7. Sorghum1 codes for the first 195 amino acids of RPL3 while sorghum2 is full-length (codes for 389 a.a. protein). The sorghum2 DNA sequence was used to produce the sorghum RPL3 protein in FIG. 8 (SEQ ID No.: 15).

Wheat (*Triticum aestivum*)

A search of the ITEC database revealed the presence of 14 ESTs derived from *T. aestivum* cDNA libraries. These ESTs fell into three classes by sequence identity. One class contained 10 members and was compiled to yield a wheat Rpl3 consensus sequence shown in FIG. 7 (SEQ ID No.: 13) (the other two classes produced short, non-overlapping consensus sequences). The wheat Rpl3 consensus sequence was composed of the following ITEC ESTs: CSB006E03F990908; AWB004.D1 OF000328; AWB005.G12F000328; MUG001.G 11R990520; MUG016.F05R990620 MUG024.B 12R990620; MUG001.H05R990428; MWL009.G10F990624; SUN004.B I1 R991213; WHE0024.D03F990702.

Corresponding amino acid sequences are shown in FIG. 8 as follows: maize (SEQ ID No.: 14), sorghum (SEQ ID No.: 15), wheat (SEQ ID No.: 16), barley (SEQ ID No.: 17) and oat (SEQ ID No.: 18) together with rice (SEQ ID No.: 3). As shown in FIG. 8, the overall amino acid sequence identity is at least 92.5% with an identical alignment between amino acid 209 and 284 (based on the rice amino acid numbering system).

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

The embodiments of the invention in which an exclusive property of privelege is claimed are defined as follows:

1. An isolated modified monocot nucleic acid, wherein the wild type form of said monocot nucleic acid encodes a ribosomal L3 protein and wherein a host cell transformed with said modified nucleic acid is resistant to trichothecene mycotoxins, wherein the modification encodes a single amino acid substitution of Cys for Trp at position 258 relative to SEQ ID NO:3.

2. The modified nucleic acid of claim 1, wherein the monocot nucleic acid encoding the ribosomal L3 protein nucleic acid is selected from the group consisting of a corn nucleic acid, a sorghum nucleic acid, a wheat nucleic acid, a barley nucleic acid and an oat nucleic acid.

3. The modified nucleic acid of claim 2, wherein the nucleic acid has a sequence which encodes the amino acid sequence selected from the group consisting of SEQ ID NO:14, SEQ ID NO:15, SEQ ID NO:16, SEQ ID NO:17 and SEQ ID NO:18, with the sequence encoding a cysteine at amino acid position 258 relative to SEQ ID NO:3.

4. A cloning vector containing the modified monocot nucleic acid as defined in claim 1.

5. The cloning vector of claim 4, wherein the monocot nucleic acid encoding the ribosomal L3 protein is selected from the group consisting of a corn nucleic acid, a sorghum nucleic acid, a wheat nucleic acid, a barley nucleic acid, and an oat nucleic acid.

6. The cloning vector of claim 5, wherein the nucleic acid has a sequence which encodes the amino acid sequence selected from the group consisting of SEQ ID NO:14, SEQ ID NO:15, SEQ ID NO:16, SEQ ID NO:17 and SEQ ID NO:18, with the sequence encoding a cysteine at amino acid position 258 relative to SEQ ID NO:3.

7. A plant transformed with the modified monocot nucleic acid of claim 1, wherein said transformed plant is resistant to trichothecene mycotoxins.

8. The plant of claim 7, wherein the nucleic acid encoding the ribosomal L3 protein is selected from the group consisting of a corn nucleic acid, a sorghum nucleic acid, a wheat nucleic acid, a barley nucleic acid and an oat nucleic acid.

9. The plant of claim 8, wherein the nucleic acid has a sequence which encodes the amino acid sequence selected from the group consisting of SEQ ID NO:14, SEQ ID NO:15, SEQ ID NO:16, SEQ ID NO:17 and SEQ ID NO:18, with the sequence encoding a cysteine at amino acid position 258 relative to SEQ ID NO:3.

10. A transformed seed from the plant of claim 7.

11. A transformed seed from the plant of claim 8.

12. A transformed seed from the plant of claim 9.

13. A method of increasing resistance to *Fusarium* species infestation by transforming a plant with the modified nucleic acid of claim 1, wherein the plant transformed with said nucleic acid has increased resistance to trichothecene mycotoxins and wherein said method comprises the steps of:

provi ding the modified nucleic acid of claim 1 and transforming a plant with said nucleic acid;

wherein the *Fusarium* species is selected from the group consisting of *F. graminearum, F. sambucinum, F. poae, F. sporotrichioides, F. culmorum* and *F. crookwellense*.

* * * * *